US012746211B2

(12) United States Patent
Wu

(10) Patent No.: US 12,746,211 B2
(45) Date of Patent: Sep. 29, 2026

(54) PARTICLE COMPOSITION COMPRISING SIALIC ACID BINDING LIGAND

(71) Applicant: Cytodigm, Inc., Natick, MA (US)

(72) Inventor: Bin Wu, Lexington, MA (US)

(73) Assignee: Cytodigm, Inc., Natick, MA (US)

( * ) Notice: Subject to any disclaimer, the term of this patent is extended or adjusted under 35 U.S.C. 154(b) by 174 days.

(21) Appl. No.: 18/533,351

(22) Filed: Dec. 8, 2023

(65) Prior Publication Data

US 2024/0358653 A1 Oct. 31, 2024

Related U.S. Application Data

(63) Continuation of application No. PCT/US2022/032674, filed on Jun. 8, 2022.

(60) Provisional application No. 63/208,150, filed on Jun. 8, 2021.

(51) Int. Cl.

*A61K 45/06* (2006.01)
*A61K 9/51* (2006.01)

(52) U.S. Cl.

CPC .......... *A61K 9/5146* (2013.01); *A61K 9/5192* (2013.01); *A61K 45/06* (2013.01)

(58) Field of Classification Search

CPC .... A61K 9/5146; A61K 9/5192; A61K 45/06; A61K 9/5089; A61K 9/5153; A61K 31/7105; A61K 9/5031; A61K 9/19; A61P 1/00

See application file for complete search history.

(56) References Cited

U.S. PATENT DOCUMENTS

| | | | |
|---|---|---|---|
| 2008/0138430 A1 | 6/2008 | Owens et al. |
| 2010/0009007 A1 | 1/2010 | Darvari et al. |
| 2010/0196280 A1 | 8/2010 | Fischer et al. |
| 2012/0294904 A1 | 11/2012 | Bader et al. |
| 2012/0294946 A1 | 11/2012 | Scott et al. |

FOREIGN PATENT DOCUMENTS

| | | |
|---|---|---|
| CA | 3138430 A1 | 12/2020 |
| WO | 2010049562 A1 | 5/2010 |
| WO | 2019086627 A1 | 5/2019 |
| WO | 2020243248 A1 | 12/2020 |

OTHER PUBLICATIONS

Bondioli, L., "PLGA Nanoparticles Surface Decorated with the Sialic Acid, N-Acetylneuraminic Acid", Biomaterials, 31(12), Apr. 2010, 3395-3403.

*Primary Examiner* — Robert A Wax
*Assistant Examiner* — Ngoc-Anh Thi Nguyen
(74) *Attorney, Agent, or Firm* — Elmore Patent Law Group, P.C.; Carolyn S. Elmore; Jia Kang

(57) ABSTRACT

This invention provides polymeric particles presenting non-conjugated sialic acid residues on their surfaces, compositions and methods of use thereof, as well as non-conjugation methods to produce nanoparticles and microparticles having sialic acid moieties on their surfaces.

22 Claims, No Drawings

PARTICLE COMPOSITION COMPRISING SIALIC ACID BINDING LIGAND

RELATED APPLICATIONS

This application is a continuation of International Application No. PCT/US22/32674, which designated the United States and was filed on Jun. 8, 2022, published in English, which claims the benefit of U.S. Provisional Application No. 63/208,150, filed on Jun. 8, 2021. The entire teachings of the above applications are incorporated herein by reference.

BACKGROUND OF THE INVENTION

Sialic acid, also known as N-acetylneuraminic acid, is a nine-carbon sugar that binds to sialic acid-binding immunoglobulin-like lectin (Siglec). Sialic acid has mainly three derivatives, N-acetyl neuraminic acid (Neu5Ac), N-acetyl neuraminic acid hydroxyalkyl (Neu5Gc) and 3-deoxy-D-glycero-D-galacto-nonyl ketose (Kdn). There are other sialic acid derivatives that are further derived from these primary derivatives. One important sialic acid derivative is ganglioside, which is found in the brain.

Siglec, which is expressed by various immune cells, has an intracellular immunoreceptor tyrosine-based inhibition motif (ITIM) that can mediate inhibitory signals upon binding to sialic acid and activate downstream inhibitory signaling through the recruitment of tyrosine phosphatases SHP-1 and SHP-2. Sialic acid can also regulate the alternative pathway of complement activation. Major serum protein complement factor H recognizes sialic acid as a "self" marker, which helps to inhibit C1q/C3b fragment activation. In addition, sialic acid also binds a carbohydrate-binding lectin overexpressed in several types of cancers.

Aberrant interactions between sialic acid and Siglec are associated with a number of pathologies including infection, autoimmunity, and cancer. It can therefore be therapeutically beneficial to bind Siglecs on certain types of cells with a chemical or biological entity that comprises sialic acid residue to modulate the immune inhibition or activation for the treatment of pathologies including infection, autoimmunity, and cancer. However, it is difficult to deliver such molecular entities of sialic acid to target cells in vivo. A common strategy is to attach the molecules of sialic acid or polysialic acid on the surface of nanoparticles so that the nanoparticles can carry the sialic acid entities to the cells of target.

Additionally, as sialic acid binds Siglecs on certain types of immune cells, chemical entities comprising sialic acid moiety can be attached on particles as ligands to guide said particles to the immune cells and cause the particles to bind the Siglecs on the cells. Such binding can facilitate the particles to enter the cell via receptor-mediated endocytosis. In this manner, nanoparticles loaded with therapeutic agents and surface-coated with sialic acid or sialic acid-containing entities can target immune cells and deliver the therapeutic agents into the cells.

Nanomedicine is an important tool in targeted drug delivery. It is desirable that systemically dosed, drug-loaded nanoparticles have a long circulation time before they reach a targeted site. The current strategy to prolong the in vivo circulation of nanoparticles is to PEGylate the surface of the particles to prevent nanoparticles from being taken up by the reticuloendothelial system (RES). However, PEGylated nanoparticles may lead to the production of PEG-specific antibodies and mitigate the drug release and target cell interaction, thus compromising the therapeutic effects.

Therefore, there is a need for developing new strategies capable of extending nanoparticle circulation in vivo while substituting polyethylene glycol (PEG).

The current method for attaching sialic acid to the surface of nanoparticles is by chemical conjugation. For example, a sialic acid molecule can be functionalized with a reactive group capable of forming a covalent bond with another reactive group on the nanoparticle surface. However, this method suffers from low conjugation efficiency and side reactions leading to undesired side-products in the pharmaceutical formulation.

Therefore, there is an unmet need for novel methods to attach ligands containing sialic acid to the surface of nanoparticles.

SUMMARY OF THE INVENTION

The present invention provides polymeric particles presenting non-conjugated sialic acid residues on their surfaces, compositions and methods of use thereof, as well as non-conjugation methods to produce nanoparticles and microparticles having sialic acid moieties on their surfaces.

The invention includes a composition comprising polymeric particles presenting sialic residues on their surfaces, wherein the particles are microparticles or nanoparticles; wherein each particle comprises a biodegradable polymer and a polysialic acid comprising the sialic acid residues, wherein the sialic acid residues are not conjugated to the surface of the particles. The biodegradable polymer is preferably a pharmaceutically acceptable biodegradable polymer. In certain aspects, the biodegradable polymer can be selected from the group consisting of polylactide (PLA), poly(lactide-co-glycolide) (PLGA), copolymers of ethylene glycol and lactide/glycolide (PEG-PLGA), copolymers of ethylene glycol and lactide (PEG-PLA), copolymers of ethylene glycol and glycolide (PEG-PGA), poly(ethylene glycol) (PEG), polycaprolactone (PCL), polyanhydrides (PANH), poly(ortho esters), polycyanoacrylates, poly(hydroxyalkanoate)s (PHAs), poly(sebasic acid), polyphosphazenes, polyphosphoesters, modified poly(saccharide)s, mixtures and copolymers thereof. In certain embodiments, the biodegradable polymer is PLGA. In additional aspects, the biodegradable polymer and the polysialic acid form an interpenetrating network. The particles can further comprise an active agent such as an active pharmaceutical ingredient.

The invention additionally encompasses a method for administration of an active agent to a subject in need thereof comprising administering to said subject the composition comprising particles presenting sialic acid residues on their surfaces, wherein the particles are microparticles or nanoparticles; wherein each particle comprises a biodegradable polymer and a polysialic acid comprising the sialic acid residues, wherein the sialic acid residues are not conjugated to the surface of the particles; and further wherein the particles comprise the active agent. The active agent can be an active pharmaceutical ingredient. In certain aspects, the active agent is encapsulated within the particles.

The invention further includes a method of treating a disease or disorder in a subject in need thereof comprising administering to the subject the particles described herein.

The invention includes a method for the preparation of microparticles or nanoparticles presenting sialic acid residue on their surfaces comprising: (1) dissolving a biodegradable polymer (and optionally an active agent, such as a pharmaceutical ingredient (API), or a poorly water soluble compound) in a first solvent to form a polymer solution; (2) emulsifying the polymer solution in a solution of a second solvent to form an emulsion, wherein the first solvent is not miscible or partially miscible with the second solvent, and wherein the solution of the second solvent comprises a polysialic acid, said solution of the second solvent optionally further comprising a surfactant and/or an API soluble in the second solvent; and (3) removing the first solvent to form said microparticles or nanoparticles having the surface sialic acid moieties.

The invention also provides a method for the preparation of microparticles or nanoparticles presenting sialic acid moieties on their surfaces, said method comprising: (1) dissolving a biodegradable polymer (and optionally an active agent, an API, or a poorly water soluble compound) in a first solvent to form a polymer solution; (2) adding a first solution of a second solvent to the polymer solution to form a mixture, wherein the first solvent is not miscible or partially miscible with the second solvent, and wherein the first solution of the second solvent optionally comprises an active agent which may be the same or different from the API dissolved in the first solvent; (3) emulsifying the mixture to form a first emulsion; (4) emulsifying the first emulsion in a second solution of the second solvent to form a second emulsion, wherein the second solution of the second solvent comprises a polysialic acid, and optionally further comprises a surfactant; and (5) removing the first solvent to form microparticles or nanoparticles having surface sialic acid moieties.

In yet other aspects, the invention is directed to particles produced by a method described herein.

Preferably, the microparticles or nanoparticles comprise an active agent, such as an active pharmaceutical ingredient (an API).

Preferably, the API is encapsulated within the microparticles or nanoparticles. In certain preferred aspects, the particle is a nanoparticle.

Alternatively or additionally, the API is covalently or ionically attached to the surface of the microparticles or nanoparticles. For example, the API can be covalently attached to the particle surface via a hydrolysable bond that facilitates in vivo release.

Preferably, the solution of the second solvent further comprises, or is saturated with, the first solvent before the polymer solution in the first solvent is added to the first solution of the second solvent during emulsification. This may be beneficial in that the polymer in the first solvent is less likely to precipitate when added to the first solution of the second solvent for emulsification. Preferably, the first solvent is ethyl acetate, and the solution of the second solvent (e.g., water or aqueous solution) comprises about 7-8% v/v of ethyl acetate.

Preferably, said microparticles and nanoparticles are based on biodegradable polymers selected from the group consisting of: polylactide (PLA), poly(lactide-co-glycolide) (PLGA), copolymers of ethylene glycol and lactide/glycolide (PEG-PLGA), copolymers of ethylene glycol and lactide (PEG-PLA), copolymers of ethylene glycol and glycolide (PEG-PGA), poly(ethylene glycol) (PEG), polycaprolactone (PCL), polyanhydrides (PANH), poly(ortho esters), polycyanoacrylates, poly(hydroxyalkanoate)s (PHAs), poly(sebasic acid), polyphosphazenes, polyphosphoesters, modified poly(saccharide)s, mixtures and copolymers thereof. In additional preferred aspects, the biodegradable polymer is PLGA. Optionally, the microparticles and nanoparticles comprise an active agent such as a drug.

In certain preferred embodiments, the particles encapsulate the active agent.

Preferably, said polysialic acid is a pharmaceutically acceptable polymer.

Preferably, said sialic acid is sialic acid, a salt, a derivative or a mimetic thereof.

Preferably, said polysialic acid is attached to the surface of the microparticles and nanoparticles by a non-chemical process, such as coating, absorption, adsorption, and emulsification.

Preferably, said polysialic acid is durably attached to the surface of the microparticles and nanoparticles and can sustain multiple washing cycles.

Preferably, said polysialic acid has a molecular weight of from 500 to 50,000,000, from 1,000 to 5,000,000, and from 2,000 to 500,000 Da.

In some embodiments, the polysialic acid is a polysialic acid comprising only sialic acid repeating units. This type of polymer is often referred as a “homopolymer.” One example of such homopolymer of polysialic acid is colominic acid, commercially available, for example, from Carbosynth, Oakbrook Terrace, IL, USA. Colominic acid, also referred to as polysialic acid, is a linear small polysaccharide containing $\alpha$-2,8-linked sialic acid (neuraminic acid) with (n=8 to >100) residues.

In some embodiments, the polysialic acid is a “copolymer” comprising sialic acid repeating units and the repeating units of at least one different chemical entity. Non-limiting examples of such copolymers include PLGA-PSia, PEG-PSia, PLGA-PEG-PSia, etc. Here, PLGA is poly(lactide-co-glycolide), PEG is polyethylene glycol and PSia is polysialic acid.

In some embodiments, the polysialic acid is an oligomer of sialic acid, such as a dimer, a trimer, a tetramer, a pentamer or a hexamer available as N-acetylneuraminic acid oligomers or their sodium salts, available from Nacalai USA, Inc., San Diego, CA, United States.

In some embodiments, the polysialic acid is a pharmaceutically acceptable polymer having a sialic acid moiety at the terminal of its chemical structure. For example, PEG-Sia, or PLGA-PEG-Sia, where Sia represents the sialic acid moiety. Polysialic acid can also be ganglioside.

DETAILED DESCRIPTION OF THE INVENTION

Overview

Because aberrant interactions between sialic acid and Siglec are associated with a number of pathologies, including infection, autoimmunity, and cancer, providing particles presenting sialic acid moieties that bind Siglecs on certain cell can be therapeutically useful. The compositions comprising the particles can, for example, be used in the treatment of pathologies including infection, autoimmunity, and cancer. In addition, the interaction between sialic acid and Siglecs on specific immune cells can be used to guide particles comprising the sialic acid residues to the immune cells. Thus, particles that comprise a therapeutic agent as well as the sialic acid moieties can be targeted to specific immune cells.

The present invention provides particles presenting non-conjugated sialic acid residues on their surfaces, compositions, and methods of use thereof as well as non-conjugation methods to produce nanoparticles and microparticles having sialic acid moieties on their surfaces. The non-conjugation methods described herein avoid the side reactions and side-products that have been observed when using conjugation methods to attach sialic acid residues to the surface of particles.

The invention described herein provides pharmaceutical formulations comprising microparticles and nanoparticles having sialic acid residues on their surfaces (with or without agent/drug/API load), as well as processes capable of producing such pharmaceutical formulations comprising microparticles and/or nanoparticles.

The invention includes methods for the preparation of that microparticles and nanoparticles presenting sialic acid residues on their surfaces, the methods comprising coprecipitation or coacervation of a hydrophobic and/or neutral biocompatible polymer, such as PLGA or PLA, and the polysialic acid. Without being bound by any theory, it is believed that the polymer backbones intertwine or interlace while in the organic phase of emulsion. Using the methods of the invention, the polysialic acid is tightly integrated into the produced microparticles or nanoparticles. Thus, preferably, the polysialic is incorporated onto said microparticles or nanoparticles and presents sialic acid residues on the surfaces of said microparticles or nanoparticles.

With the invention generally described above, specific aspects of the invention are described further in the sections below.

Definitions

As used herein, "pharmaceutically acceptable" includes those compounds, materials, compositions, and/or dosage forms which are, within the scope of sound medical judgment, suitable for medical or veterinary use when in contact with the tissues of human beings and animals at the concentration, dosage or amount present in the product, without causing excessive toxicity, irritation, allergic response, or other problems or complications, commensurate with a reasonable benefit/risk ratio. Preferably, a pharmaceutically acceptable material (e.g., polymer, excipient, surfactant, solvent, or microparticles/nanoparticles produced therefrom) is suitable or approved for human medical use.

As used herein, "microparticles" are preferably roughly round, sphere, or sphere-like in shape, and are generally within the size range of, e.g., between about 1-1,000 μm, or between about 10-100 μm, as measured by laser diffraction, for example. The subject microparticles may also include particles that are less likely to clump or aggregate in vivo. However, it is understood that other particle morphologies are possible as well, including rods, plates, sheets, and needles. Typically, it is understood that the particle size reflects the volume median geometric size of the product sample tested.

As used herein, "nanoparticles" are preferably roughly round, sphere, or sphere-like in shape, and are generally within the size range of, e.g., between about 1-1,000 nm, between about 10-1,000 nm, or between about 50-1,000 nm, or between about 100-500 nm, as measured by laser diffraction, for example. The subject nanoparticles may also include particles that are less likely to clump in vivo.

Particle size and size distribution can be measured by a dynamic light scattering instrument, e.g., a Malvern Zetasizer. Alternative techniques include, for example, sedimentation field flow fractionation, photon correlation spectroscopy, light scattering, dynamic light scattering, light diffraction, and disk centrifugation. The terms "microparticle" and "nanoparticle" are not intended to convey any specific shape limitation. Such particles include, but are not limited to, those having a generally polyhedral or spherical geometry. Preferred particles are characterized by a spherical geometry typically produced by emulsion-based encapsulation processes. It is understood that the terms "microparticle" and "nanoparticle" are used interchangeably herein, unless accompanied by a specific description of size. For example, the term "microparticles" is intended to also embrace "nanoparticles" as if stated as "microparticles and/or nanoparticles" unless the context demands otherwise.

It is not necessary that each microparticle or nanoparticle be uniform in size, although they are generally of a size sufficient to trigger phagocytosis in an antigen presenting cell (APC) or other MPS cell. Preferably, the subject microparticles and nanoparticles have a diameter sufficient to trigger phagocytosis in an antigen presenting cell (APC) or other MPS cell.

The term "particle" encompasses both nanoparticle and microparticles. As used herein "a" or "an" means one or more unless otherwise specified.

As used herein, "about" generally means up to +10% of the particular term being modified.

As used herein the term "encapsulates", "encapsulated," and the like when referring to the drug or active agent being encapsulated within the particles means that the drug or active agent is more likely found within the microparticle than on the surface of the microparticle.

A "polysialic acid" is a polymer comprising sialic acid monomers. Polysialic acids are described in more detail below.

The terms "sialic acid residue" and "sialic acid moiety" as well as their plural referents, and the like, are used interchangeably herein.

As used herein, "conjugation" or "conjugated," and the like, in the context of a sialic acid moiety on the surface of the particle(s) refers to the covalent association of the sialic acid moiety (for example, a sialic acid moiety of a polysialic acid) to the particle or biodegradable polymer by formation of a covalent bond, for example, via a linker moiety or functionalization of the sialic acid residue with a reactive group capable of forming a covalent bond with a reactive group on the nanoparticle surface (e.g., a reactive group of the biodegradable polymer). For example, conjugation has been described using thioderivatives of polysialic acid (Bondioli et. al (2010). PLGA nanoparticles surface decorated with the sialic acid, N-acetylneuraminic acid. Biomaterials. 31. 3395-403. 10.1016/j.biomaterials.2010.01.049). Thus "not conjugated" or "non-conjugated," and the like, in the context of sialic acid residues on the surface of the particle(s) mean that the sialic acid residue(s) or the polysialic acid comprising the sialic acid residues is not covalently associated with the particle or biodegradable polymer by formation of a covalent bond therebetween. For example, the polysialic acid is attached to the surface of the microparticles and nanoparticles by a process such as coating, absorption, adsorption, and/or emulsification. Without wishing to be bound by theory, it is believed that the biodegradable polymer, such as PLGA, and polysialic acid form an interpenetrating network presenting sialic acid residues on the surface of the formed particles.

As used herein, the term "subject" is used to mean an animal, preferably a mammal, including a human or non-human. The terms "patient" and "subject" may be used herein interchangeably.

"Treatment" or "therapy" of a subject refers to any type of intervention or process performed on, or the administration of an active agent to, the subject with the objective of reversing, alleviating, ameliorating, inhibiting, slowing own or preventing the onset, progression, development, severity or recurrence of a symptom, complication, condition or biochemical indicia associated with a disease. As used herein, "treatment" (and grammatical variations thereof such as "treat" or "treating") includes to clinical intervention to alter the natural course of a disease in the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, combinations of the invention are used to delay development of a disease or to slow the progression of a disease.

Biodegradable Polymer

A biodegradable polymer is a polymer that can be metabolized or decomposed by a living thing. In certain aspects, the biodegradable polymer is decomposed or is metabolized without causing substantial toxic effects. The biodegradable polymer of the current invention can be selected from the group consisting of: polylactide (PLA), poly(lactide-co-glycolide) (PLGA), copolymers of ethylene glycol and lactide/glycolide (PEG-PLGA), copolymers of ethylene glycol and lactide (PEG-PLA), copolymers of ethylene glycol and glycolide (PEG-PGA), poly(ethylene glycol) (PEG), polycaprolactone (PCL), polyanhydrides (PANH), poly(ortho esters), polycyanoacrylates, poly(hydroxyalkanoate)s (PHAs), poly(sebasic acid), polyphosphazenes, polyphosphoesters, modified poly(saccharide)s, mixtures and copolymers thereof. PLGA is a preferred biodegradable polymer in this invention.

PLGA

PLGA is typically prepared by ring-opening polymerization of lactide and glycolide. In this reaction, Stannous octoate is usually used as the catalyst, although other catalysts may also be used. An initiator, such as an alcohol, is often used to initiate the polymerization reaction. If no initiator is intentionally added, trace amount of polar compound containing an active proton, such as alcohol and water, may serve as the initiator. Polymerization usually results in a PLGA polymer with a carboxyl group at the chain terminal, as illustrated below:

R—OH+L (lactide monomer)+G (glycolide monomer)=PLGA-COOH

Therefore, each PLGA and/or PLA polymer molecule is typically linear, and typically contains a single COOH group at the chain terminal. In addition, there may not be sufficient numbers of COOH groups for covalently attaching APIs or other chemical moiety such as protein ligands or other targeting agents to the surface of said microparticles and nanoparticles. Such protein ligands or other targeting agents may bind to a receptor or a binding partner on the surface of a target cell, tissue, organ, or location.

The instant invention provides various methods or combinations thereof for producing PLGA/PLA particles with polysialic acid. Such particles are particularly useful, for example, to treat certain diseases (such as inflammatory diseases, autoimmune disease, and cancer) and for delivering an active agent.

Preferably, the average molecular weight of the pharmaceutically acceptable polymer PLGA is within a desired range.

The low end of the range is preferably no less than about 100, 200, 300, 400, 500, 600, 700, 800, 900, 1000, 1200, 1500, 2000, 2500, or 3000 Da. The desired range has a low end of any of the above values.

The high end of the range is preferably no more than 50,000, 40,000, 35,000, 30,000, 25,000, 20,000, 15,000, 10,000, 7,500, or 5,000 Da. The desired range has a high end of any of the above values.

For instance, the desired range may be from about 500 to about 50,000 Da, or from about 1,000 to about 30,000 Da.

Preferably, the PLGA has an average molecular weight of from about 500 to about 1,000,000 Da, preferably from about 1,000 to about 50,000 Da.

The PLGA can contain multiple negatively charged terminal groups.

For PLGA, average molecular weight can be expressed in other physical properties such as inherent viscosity. Inherent Viscosity (IV) is a viscometric method for measuring molecular size. IV is based on the flow time of a polymer solution through a narrow capillary relative to the flow time of the pure solvent through the capillary. For certainty measures in the instant application, the solvent used is typically chloroform, and the polymer concentration is about 0.5% (w/v). The temperature at which the viscosity is measured is about 30° C. The units of IV are typically reported in deciliters per gram (dL/g). Thus, for example, PLGA used in the instant invention may have an inherent viscosity of from about 0.01 to about 20 dL/g, or from about 0.05 to about 2.0 dL/g.

The composition and biodegradability of the subject PLGA polymer is partly determined by the molar ratio of lactide (L) to glycolide (G) unit in the polymer, or L/G ratio. The L/G ratio of the PLGA polymer in the present invention can be from 100/0 to 0/100. As used herein, an L/G ratio of "100/0" refers to polylactide or PLA, and an L/G ratio of "0/100" refers to polyglycolide, or PGA. Preferably, the L/G ratio for the PLGA polymer is from about 100/0 to 0/100, or about 95/5 to 5/95, more preferably from about 85/15 to 15/85. The most preferable L/G ratio in the present invention is about 50/50.

Other polymers can be mixed with the PLGA polymer in the preparation of the PLGA microparticles and nanoparticles. For example, polyethylene glycol, or PEG, is often added to the PLGA for enhanced performance. PEGylated particles are useful because they often have increased circulation time in human or animal bodies.

Preferably, copolymers of PEG and PLGA can also be used.

The microparticles and nanoparticles prepared from the PEG and PLGA mixture or PEG and PLGA copolymer are referred to as PEGylated PLGA microparticles and nanoparticles.

Such "PEGylation" process can also be done after microparticles and nanoparticles are formed. In this case, PEG polymers or other polymers containing PEG units are coated via physical absorption onto the PLGA microparticles and nanoparticles.

The PEG units can also be attached to the surface of PLGA microparticles or nanoparticles via covalent bonds. Such process is often referred to as "conjugation." In a conjugation process, a reactive entity containing PEG units react with certain functional groups on the surface of the microparticles and nanoparticles to form chemical bonds.

Thus, preferably, the pharmaceutically acceptable polymer is PLGA, and the microparticles or nanoparticles are PEGylated. The microparticles or nanoparticles may be PEGylated by mixing polyethylene glycol (PEG) or PEG-containing entity during the preparation of the microparticles and nanoparticles. The microparticles or nanoparticles may also be PEGylated by using copolymers of PEG and PLGA. The microparticles or nanoparticles can further be PEGylated by physically absorbing PEG polymers or polymers containing PEG units onto the PLGA microparticles and nanoparticles. The microparticles or nanoparticles may additionally be PEGylated by conjugating PEG units to the surface of the PLGA microparticles or nanoparticles via covalent bonds.

Preferably, the biodegradable polymer has an average molecular weight of from about 500 to about 1,000,000 Da, preferably from about 1,000 to about 200,000 Da.

Preferably, the biodegradable polymer is PLGA and has an L/G ratio of from about 100/0 to 0/100, about 95/5 to 5/95, about 85/15 to 15/85, and about 50/50.

Polysialic Acid

Polysialic acid (PSia) includes homopolymers of sialic acid. Naturally occurring PSia was first found in *E. coli* and is one of the ingredients of bacterial capsular materials, such as *Neisseria miningitidis B, Salmonella toucra* 048 and *Citrobacter freundii* 05. PSia can be in a conformation of α-2,8 (A in the figure below) or α-2,9 linkages (B in the figure below) or a mixture of α-2,8 and α-2,9. PSia constituted of α-2,8 bond is non-immunogenic and biodegradable and can reduce the immunogenicity of protein polypeptides. PSia possess the properties of escaping phagocytes and prolonging circulation time in vivo.

A

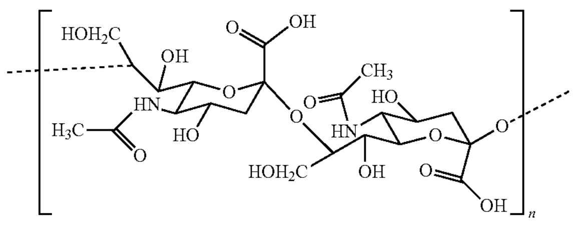

B

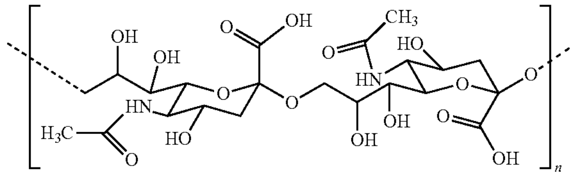

Therefore nanoparticles having a sialic acid moiety on the surface may also facilitate RES escape and render the nanoparticles and microparticles prolonged circulation in the bloodstream. In addition, since sialic acid also binds several receptors on tumor cells, sialic acid-coated nanoparticles and microparticles can be leveraged to target tumor site via the high-avidity binding of sialic acid to lectins.

As described above, a polysialic acid is a polymer comprising a chain of sialic acid monomers. In certain aspects, the polymer is a homopolymer (e.g., all the sialic acid monomerunits are the same). In other aspects, the polymer is a heteropolymer (e.g., the polysialic acid comprises at least two different sialic acid monomer units). In yet other aspects, the polymer comprises at least 10, at least 15, at least 20, at least 30, at least 40, at least 50, at least 60, at least 75, at least 100, at least 200, or at least 300 sialic acid monomers. The sialic acid monomer can be any derivative of a neuraminic acid. Sialic acid monomers include, for example, N-acetylneuraminic acid (Neu5Ac), N-glycolylneuraminic acid (Neu5Gc), or deaminated neuraminic acid (Kdn; 3-deoxy-D-glycero-D-galactononulosonic acid. The sialic acid monomer is exemplified by Formula (I):

(I)

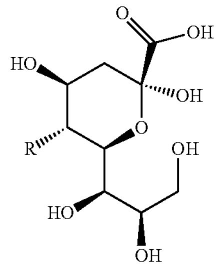

In Neu5Ac, R is —NH—C(O)—CH3. In Neu5Gc, R is —NH—C(O)—CH2-OH. In Kdn, R is OH. Other examples of sialic acid monomers are N-sialic acid, 0-sialic acid, 9-O-acetyl-8-O-methyl-N-acetylneuraminic acid (Neu5, 9Ac28Me), and 7,8,9-tri-O-acetyl-N-glycolylneuraminic acid (Neu5Gc7,8,9Ac3), Neu4,5Ac2; Neu5,7Ac2; Neu5, 8Ac2; Neu5,9Ac2; Neu4,5,9Ac 3; Neu5,7,9Ac 3; Neu5,8, 9Ac 3; Neu5,7,8,9Ac 4; Neu5Ac9Lt; Neu4,5Ac 29Lt; Neu5Ac8Me; Neu5,9Ac28Me; Neu5Ac8S; Neu5Ac9P; Neu2en5Ac; Neu2en5,9Ac 2; Neu2en5Ac9Lt; Neu2, 7an5Ac; Neu5Ge; Neu4Ac5Gc; Neu7Ac5Gc; Neu8Ac5Gc; Neu9Ac5Gc; Neu7,9Ac 25Gc; Neu8,9Ac 25Gc; Neu7,8, 9Ac 35Gc; Neu5Gc9Lt; Neu5Gc8Me; Neu9Ac5Gc8Me; Neu7,9Ac 25Gc8Me; Neu5Gc8S; Neu5GcAc; Neu5GcMe; Neu2en5Gc; Neu2en9Ac5Gc; Neu2en5Gc9Lt; Neu2en5Gc8Me; Neu2,7an5Gc; Neu2,7an5Gc8Me; and Knd9Ac.

As described above, sialic acid monomers can be joined by α-2,8-, α-2,9, or α-2,8/α-2-9-ketosidic linkages, for example, α-2,4-ketosidic linkages and α-2,5-ketosidic linkages have also been described (Janas et al. (2011), Biochimica et Biophysica Acta 1808: 2923-2932). The sialic acid monomers can be joined in any bonding arrangement. In certain embodiments, the polysialic acid comprises monomers that are 248 linked, 2→9 linked, or a combination thereof. In yet other aspects, the monomers are all 248 linked or all 2→9 linked. In further aspects, the polysialic acid comprises Neu5Ac monomers that are 248 linked, 2→9 linked, or a combination thereof. In yet other aspects, the polysialic acid comprises Neu5Gc monomers that are 248 linked, 2→9 linked, or a combination thereof. In further embodiments, the polysialic acid comprises Kdn monomers that are 248 linked, 2→9 linked, or a combination thereof. The polysialic acid can be a homopolymer comprising monomers selected from Neu5Ac, Neu5Gc, and Kdn, or the polysialic acid can be a heteropolymer comprising 2 or 3 monomers selected from Neu5Ac, Neu5Gc, and Kdn. In certain specific embodiments, the homopolymer comprises Neu5Ac monomers. The homopolymer can be a poly (Neu5Ac)n, a poly(Neu5Gc)n, or a poly(Kdn)n polymer, wherein n is an integer greater than 10, greater than 15, or greater than 20; and optionally, wherein the monomers are 2→8 linked, 2→9 linked, or a combination thereof. In yet other specific embodiments, the heteropolymer comprising Neu5Ac and Neu5Gc monomers.

The polysialic acid can be a branched or unbranched polymer. An "unbranched" polymer is straight-chain polysialic acid polymer comprising a linear sequence of monomers. A "branched" polymer is a polysialic acid polymer that comprises a main chain with one more substituent side chains or branched. An example of a branched polymer is one that comprises a sialic acid unit bonded to three or more different sialic acid units, thereby creating a branch point within the polysialic acid.

The polysialic acid can, for example, have a molecular weight of at least 1 kDa, at least 3 kDa, at least 5 kDa, at least 10 kDa, at least 20 kDa, at least 25 kDa, at least 30 kDa, at least 40 kDa, at least 50 kDa, at least 60 kDa, at least 70 kDa, at least 75 kDa, at least 80 kDa, at least 90 kDa, at least 100 kDa, etc.

Preferably, said polysialic acid has a molecular weight of from 500 to 50,000,000, from 1,000 to 5,000,000, or from 2,000 to 500,000 Da.

In some embodiments, the polysialic acid is a polysialic acid comprising only sialic acid repeating units. This type of polymer is often referred as a "homopolymer." One example of such homopolymer of polysialic acid is colominic acid, commercially available from Carbosynth, Oakbrook Terrace, IL, USA. Colominic acid, also referred as polysialic acid, is a linear small polysaccharide containing α-2,8-linked sialic acid (neuraminic acid) with (n=8 to >100) residues.

In some embodiment, the polysialic acid is a "copolymer" comprising sialic acid repeating units and the repeating units of at least one different chemical entity. Non-limiting examples of such copolymers include PLGA-PSia, PEG-PSia, PLGA-PEG-PSia, etc. Here, PLGA is poly(lactide-co-glycolide), PEG is polyethylene glycol and PSia is polysialic acid. The polysialic acid can also be ganglioside.

In some embodiment, said polysialic acid is an oligomer of sialic acid, such as a dimer, a trimer, a tetramer, a pentamer and a hexamer available as N-acetylneuraminic acid oligomers or their sodium salts, available from Nacalai USA, Inc., San Diego, CA, United States.

In some embodiment, said polysialic acid is a pharmaceutically acceptable polymer having a sialic acid moiety at the terminal of its chemical structure. For example, PEG-Sia, or PLGA-PEG-Sia, where Sia represents the sialic acid moiety.

The sialic acid can also be a water-soluble salt and water-soluble derivative of sialic acid. For example, the sialic acid salt can be the sodium salt, the potassium salt, the magnesium salt, the calcium salt, or the zinc salt. As described above, the polysialic acid can comprising a combination of more than one type of sialic acid.

In one set of embodiments, one or more of sialic acid monomers within the polysialic acid is modified. For example, one or more sialic acid units can be modified by attachment to polyethylene glycol, or an alkyl group. In other embodiments, the polysialic acid is not modified.

The polysialic acid can also comprise other monomers or units in addition to sialic acid monomer. In certain examples, the polysialic acid is a conjugate of a polymer of sialic acid monomer units and another polymer, for example, a synthetic polymer, including for example, polyethylene glycol (PEG) (e.g., a polysialic acid-PEG copolymer). An example of such a conjugate has been described, for example, in Zhang et al. (2018), Drug Delivery and Translational Research 8, 602-616. The PEG can have the formula: H—(O—CH2-CH2)n-OH, where n is an integer representing the PEG polymerization degree. For example, n is at least 2, at least 4, at least 6, at least 8, at least 10, at least 15, at least 20, at least 25, at least 30, at least 40, at least 50, at least 75, at least 100, at least 200, at least 300, at least 400, or at least 500. In some cases, n is no more than 1000, no more than 500, no more than 200, no more than 100, no more than 50, no more than 30, or no more than 10.

The polysialic acids in a particle can be the same or can be different.

In addition, the polysialic acid can be substituted covalently or ionically along the length of the chain or at the termini of the chain. For example, one or more monomer units can be substituted by a targeting moiety, such as a cell ligand (or fragment), peptide, or carbohydrate. The substitution or conjugation step of the targeting moiety can occur before the microparticle is formed or after.

In some examples, the amount of the polysialic acid used in the current invention can be from 0.01% to 30%, preferably from 0.1% to 15%, based on the weight of the PLGA used in the formulation.

Active Agent

The particles described can further comprise an active agent. The composition can comprise an API, and the API can be covalently or ionically attached to the surface of the microparticles or nanoparticles via covalent bonds, such as a bond formed between an amide group of a protein and a carboxyl group on the surface of the microparticle or nanoparticle. The API can also be encapsulated within the microparticles or nanoparticles. The amount of the API can be about 0.01 to about 50% (w/w) of the microparticle or nanoparticle, or about 0.05 to about 25%, about 0.1 to about 10%, about 0.2 to about 5%, about 0.5 to about 3%, about 1 to about 5%, or about 2 to about 5% (w/w) of the microparticle or nanoparticle.

In certain aspects, the active agent is advantageously a drug (also referred to herein as an active pharmaceutical ingredient, or API). However, active agents that are non-therapeutic can also be included as part of the particles according to the methods. For example, agents useful in diagnostics, agriculture, cosmetics, personal products, home products, industrial chemicals, dyes, fluorescing agents or coloring agents and the like can be included. Preferred active ingredients include small molecules and macromolecules. For example, biomolecules, such as peptides, peptidomimetics, oligonucleotides, nucleic acid molecules and mimics thereof, such as DNA, RNA, PNA, siRNA, microRNA, antisense, proteins, antibodies and antigen binding fragments thereof, enzymes, hormones, growth factors, antigens, neoantigens, saccharides, oligosaccharides, polysaccharides, and a combination thereof. The composition can be free from other active pharmaceutical ingredients or API, such as attached peptide or antigenic moieties. It is understood that an API can be substituted with non-therapeutic compounds, such as diagnostic, agricultural, or chemical agents. Therefore, in each instance where the term API is used, it shall be understood that the term "active agent," including diagnostic, agricultural or chemical agents can be used in lieu thereof. The term "API" and "drug" are used interchangeably herein.

The API can be water-soluble or have relatively poor water-solubility. For example, a poorly water-soluble API may be dissolved in the same first solvent used to dissolve PLGA, or be dissolved in a suitable solvent (that may be the same or different from the first solvent) to form an API solution, before the API solution is mixed with the first solvent comprising PLGA, such that the API and PLGA both remain in the resulting solution. A water-soluble API may be first dissolved in its own solvent (that may be the same or different from the $2^{nd}$ solvent) to form an API solution, before the API solution is added to the second solvent.

An API or active agent can include a wide variety of different compounds, including chemical compounds and mixtures of chemical compounds, e.g., small organic or inorganic molecules; saccharins; oligosaccharides; polysaccharides; biological macromolecules, e.g., peptides, proteins, and peptide analogs and derivatives; peptidomimetics; antibodies and antigen binding fragments thereof, nucleic acids; nucleic acid analogs and derivatives; an extract made from biological materials such as bacteria, plants, fungi, or animal cells; animal tissues; naturally occurring or synthetic compositions; and any combinations thereof. Preferably, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

As used herein a "peptide" is an oligopeptide, for example, a sequence of 2 to 25 amino acids. The term "peptide", unless otherwise specified, includes in its scope a peptide that contains an already known analog of a naturally-occurring amino acid having a function as well as the naturally-occurring amino acid. A "protein" comprises one or more peptide (polypeptide) chains and can comprise more amino acids than a peptide. The terms "peptide," "polypeptide," and "protein," may be used interchangeably herein.

Exemplary therapeutic agents include, but are not limited to, those approved by the FDA, subject to a new drug application with the FDA, in clinical trials or in preclinical research.

APIs include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an anti-parkinsonian agent, an anti-angina/antihypertensive agent, an anticoagulant agent, an antiplatelet agent, a sedative, an anxiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; anti-inflammatory agents, including anti-asthmatic anti-inflammatory agents, anti-arthritis anti-inflammatory agents, and non-steroidal anti-inflammatory agents, examples of which include but are not limited to sulfides, mesalamine, budesonide, salazopyrin, diclofenac, pharmaceutically acceptable diclofenac salts, nimesulide, naproxen, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; anti-angina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Examples of suitable APIs include infliximab, etanercept, bevacizumab, ranibizumab, adalimumab, certolizumab pegol, golimumab, Interleukin 1 (IL-1) blockers such as anakinra, T cell costimulation blockers such as abatacept, Interleukin 6 (IL-6) blockers such as tocilizumab; Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/.beta.2blockers such as Anti-lymphotoxin alpha (LTa) or anti-VEGF agents and the like.

Drugs or API include proteins or peptides, including but not limited, monoclonal antibodies (e.g., humanized, human, and/or mouse/human chimeric), polyclonal antibodies, and antibody-drug conjugates. Exemplary peptide/protein therapeutics include insulin, etanercept, pegfilgrastim, salmon calcitonin, cyclosporine, octreotide, liraglutide, bivalirudin, desmopressin, C1 esterase inhibitor (RUCONSET®), human glucocerebrosidase (ELELYSO®), humanized anti-CD20 monoclonal antibody (GAVYZA®), VEGFR Fc-fusion (EYLEA®), glucagon-like peptide-1 receptor agonist Fc-fusion (TRULICITY®), VEGFR Fc-fusion (ZALTRAP), Recombinant factor IX Fc fusion (AL- PROLIX), Recombinant factor VIII Fc-fusion (ELOCTATE), GLP-1 receptor agonist-albumin fusion (TANZEUM®), Recombinant factor IX albumin fusion (IDELIVION®), PEGylated IFNb-1a (PLEGRIDY®), Recombinant factor VIII PEGylated (ADYNOVATE®), humanized anti-HER2/neu conjugated to emtansine (KADCYLA®), belimumab, ipilimumab, belatacept, brentuximab vedotin, aflibercept, asparaginase erwinia chrsanthemi, glucarpidase, taliglucerase alfa, pertuzumab, ziv-afilbercept, tbo-filgrastm, ocriplasmin, raxibacumab, ado-trastuzmab emtansine, golimumab, tocilizumab, Obinutuzumab, elosulfase alfa, metreleptin, albiglutide, ramucirumab, siltuxiumab, vedolizumab, peginterferon beta-1a, pembrolizumab, dulaglutide, bintumomab, nivolumab, secukinumab, parathyroid hormone, filgrastim-sndz, dinutuximab, alirocumab, evolocumab, idaracizumab, asfotase-alfa, mepolizumab, dratumumab, necitumumab, elotuzumab, sebelipase alfa, obiltoxaximab, ixekizumab, reslizumab, infliximab-dyyb, atezolizumab, daclizumab, etancerpt-szzs, coagulation factor IX recombinant human, antihemophilic factor (recombinant), coagulation factor XIII A-subunit (recombinant), coagulation factor IX (recombinant), Fc fusion protein, antihemophilic factor (recombinant), Fc fusion protein, C1 esterase inhibitor recombinant, antihemophilic factor porcine, B-domain truncated recombinant, coagulation factor IX (recombinant), antihemophilic factor (recombinant), antihemophilic factor (recombinant) PEGylated, von Willebrand factor (recombinant), coagulation factor IX recombinant human, and antihemophilic factor (recombinant).

The present invention is particularly applicable to the administration of anti-cancer agents. For example, the agent can be a DNA demethylating agents 5-azacytidine (azacitidine) or 5-aza-2'-deoxycytidine (decitabine), (Cytarabine or ara-C); pseudoiso-cytidine (psi ICR); 5-fluoro-2'-deoxycytidine (FCdR); 2'-deoxy-2', 2'-difluorocytidine (Gemcitabine); 5-aza-2'-deoxy-2', 2'-difluorocytidine; 5-aza-2'-deoxy-2'-fluorocytidine; Zebularine; 2', 3'-dideoxy-5-fluoro-3'-thiacytidine (Emtriva); 2'-cyclocytidine (Ancitabine); Fazarabine or ara-AC; 6-azacytidine (6-aza-CR); 5,6-dihydro-5-azacytidine (dH-aza-CR); N.sup.4-pentyloxy-carbonyl-5'-deoxy-5-fluorocytidine (Capecitabine); $N^4$-octadecyl-cytarabine; or elaidic acid cytarabine. The cytidine analog can also be structurally related to cytidine or deoxycytidine and functionally mimics and/or antagonizes the action of cytidine or deoxycytidine. The agents can also include 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyano-morpholino doxorubicin, doxorubicin glucuronide, endostatin, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3', 5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethylauristatin E (MMAE), navelbine, neratinib, nilotinib, nitrosurea, olaparib, plicomycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839 or a pharmaceutically acceptable salt thereof.

The anticancer agents include, but are not limited to, an inhibitor, agonist, antagonist, ligand, modulator, stimulator, blocker, activator or suppressor of a gene, ligand, receptor, protein, factor such as an adenosine receptor (such as A2B, A2a, A3), Abelson murine leukemia viral oncogene homolog 1 gene (ABL, such as ABL1), Acetyl-CoA carboxylase (such as ACC1/2), adrenocorticotropic hormone receptor (ACTH), activated CDC kinase (ACK, such as ACK1), Adenosine deaminase, Adenylate cyclase, ADP ribosyl cyclase-1, Aerolysin, Angiotensinogen (AGT) gene, murine thymoma viral oncogene homolog 1 (AKT) protein kinase (such as AKT1, AKT2, AKT3), AKT1 gene, Alkaline phosphatase, Alpha 1 adrenoceptor, Alpha 2 adrenoceptor, Alpha-ketoglutarate dehydrogenase (KGDH), Aminopeptidase N, Arginine deiminase, Beta adrenoceptor, Anaplastic lymphoma kinase receptor, anaplastic lymphoma kinase (ALK, such as ALK1), Alk-5 protein kinase, AMP activated protein kinase, Androgen receptor, Angiopoietin (such as ligand-1, ligand-2), apolipoprotein A-I (APOA1) gene, apoptosis signal-regulating kinase (ASK, such as ASK1), Apoptosis inducing factor, apoptosis protein (such as 1, 2), Arginase (I), asparaginase, Asteroid homolog 1 (ASTE1) gene, ataxia telangiectasia and Rad 3 related (ATR) serine/threonine protein kinase, Axl tyrosine kinase receptor, Aromatase, Aurora protein kinase (such as 1, 2), Basigin, BCR (breakpoint cluster region) protein and gene, B-cell lymphoma 2 (BCL2) gene, Bc12 protein, Bc12 binding component 3, BCL2L11 gene, Baculoviral IAP repeat containing 5 (BIRCS) gene, B-Raf proto-oncogene (BRAF), Brc-Abl tyrosine kinase, Beta-catenin, B-lymphocyte antigen CD19, B-lymphocyte antigen CD20, B-lymphocyte stimulator ligand, B-lymphocyte cell adhesion molecule, Bone morphogenetic protein-10 ligand, Bone morphogenetic protein-9 ligand modulator, Brachyury protein, Bradykinin receptor, Bruton's tyrosine kinase (BTK), Bromodomain and external domain (BET) bromodomain containing protein (such as BRD2, BRD3, BRD4), Calmodulin, calmodulin-dependent protein kinase (CaMK, such as CAMKII), Cancer testis antigen 2, Cancer testis antigen NY-ESO-1, Cannabinoid receptor (such as CB1, CB2), Carbonic anhydrase, caspase 8 apoptosis-related cysteine peptidase CASP8-FADD-like regulator, Caspase (such as caspase-3, caspase-7, Caspase-9), Caspase recruitment domain protein-15, Cathepsin G, chemokine (C—C motif) receptor (such as CCR2, CCR4, CCR5), CCR5 gene, Chemokine CC21 ligand, cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; Chorionic gonadotropin, Cyclin G1, Cyclin D1, cyclin-dependent kinases (CDK, such as CDK1, CDK1B, CDK2-9), casein kinase (CK, such as CM, CMI), c-Kit (tyrosine-protein kinase Kit or CD117), c-Met (hepatocyte growth factor receptor (HGFR)), CDK-activating kinase (CAK), Checkpoint kinase (such as CHK1, CHK2), Cholecystokinin CCK2 receptor, Claudin (such as 6, 18), Clusterin, Complement C3, COP9 signalosome subunit 5, CSF-1 (colony-stimulating factor 1 receptor), CSF2 gene, clusterin (CLU) gene, Connective tissue growth factor, cyclooxygenase (such as 1, 2), cancer/testis antigen 1B (CTAG1) gene, CTLA-4 (cytotoxic T-lymphocyte protein 4) receptor, CYP2B1 gene, Cysteine palmitoyltransferase porcupine, cytokine signalling-1, cytokine signalling-3, Cytochrome P450 11B2, Cytochrome P450 reductase, cytochrome P450 3A4, cytochrome P450 17A1, Cytochrome P450 17, Cytochrome P450 2D6, (provided the anticancer or cytrochrome modifying agents are something other than cobicistat), Cytoplasmic isocitrate dehydrogenase, Cytosine deaminase, cytosine DNA methyltransferase, cytotoxic T-lymphocyte protein-4, chemokine (C—X—C motif) receptor (such as CXCR4, CXCR1 and CXCR2), Delta-like protein ligand (such as 3, 4), Deoxyribonuclease, Dickkopf-1 ligand, Dihydropyrimidine dehydrogenase, DNA binding protein (such as HU-beta), DNA dependent protein kinase, DNA gyrase, DNA methyltransferase, DNA polymerase (such as alpha), DNA primase, discoidin domain receptor (DDR, such as DDR1), DDR2 gene, dihydrofolate reductase (DHFR), Dipeptidyl peptidase IV, L-dopachrome tautomerase, dUTP pyrophosphatase, echinoderm microtubule like protein 4, epidermal growth factor receptor (EGFR) gene, EGFR tyrosine kinase receptor, Eukaryotic translation initiation factor 5A (EIFSA) gene, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), epidermal growth factor, epidermal growth factor receptors (EGFR), Epithelial cell adhesion molecule (EpCAM), Ephrin (EPH) tyrosine kinase (such as Epha3, Ephb4), Ephrin B2 ligand, Epigen, Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, Extracellular signal-regulated kinases (ERK), E-selectin, Estradiol 17 beta dehydrogenase, Estrogen receptor (such as alpha, beta), Estrogen related receptor, Exportin 1, Extracellular signal related kinase (such as 1, 2), Factor (such as Xa, VIIa), Fas ligand, Fatty acid synthase, Ferritin, focal adhesion kinase (FAK, such as FAK2), fibroblast growth factor (FGF, such as FGF1, FGF2, FGF4), FGF-2 ligand, FGF-5 ligand, Fibronectin, Fms-related tyrosine kinase 3 (Flt3), farnesoid×receptor (FXR), Folate, Folate transporter 1, Folate receptor (such as alpha), folate hydrolase prostate-specific membrane antigen 1 (FOLH1), paired basic amino acid cleaving enzyme (FURIN), FYN tyrosine kinase, Galactosyltransferase, Galectin-3, glucocorticoid-induced TNFR-related protein GITR receptor, Glucocorticoid, Beta-glucuronidase, Glutamate carboxypeptidase II, glutaminase, Glutathione S-transferase P, Glypican 3 (GPC3), glycogen synthase kinase (GSK, such as 3-beta), Granulocyte-colony stimulating factor (GCSF) ligand, Granulocyte macrophage colony stimulating factor (GM-CSF) receptor, gonadotropin-releasing hormone (GNRH), growth factor receptor-bound protein 2 (GRB2), molecular chaperone groEL2 gene, Grp78 (78 kDa glucose-regulated protein) calcium binding protein, Imprinted Maternally Expressed Transcript (H19) gene, Heat stable enterotoxin receptor, Heparanase, Hepatocyte growth factor, Heat shock protein gene, Heat shock protein (such as 27, 70, 90 alpha, beta), Hedgehog protein, HERV-H LTR associating protein 2, Hexose kinase, tyrosine-protein kinase HCK, Histamine H2 receptor, histone deacetylase (HDAC, such as 1, 2, 3, 6, 10, 11), Histone H1, Histone H3, Histone methyltransferase (DOT1L), Human leukocyte antigen (HLA), HLA class I antigen (A-2 alpha), HLA class II antigen, Homeobox protein NANOG, mitogen-activated protein kinase kinase 1 (MAP4KI, HPK1), HSPB1 gene, Human papillomavirus (such as E6, E7) protein, Hyaluronidase, Hyaluronic acid, Hypoxia inducible factor-1 alpha, Intercellular adhesion molecule 1 (ICAM-1), immunoglobulin (such as G, G1, G2, K, M), indoleamine 2,3-dioxygenase (IDO, such as IDO1), indoleamine pyrrole 2,3-dioxygenase 1 inhibitor, I-Kappa-B kinase (IKK, such as IKK.beta..epsilon.), Immunoglobulin Fc receptor, Immunoglobulin gamma Fc receptor (such as I, III, IIIA), Interleukin 1 ligand, interleukin 2 ligand, Interleukin-2, IL-2 gene, IL-1 alpha, IL-1 beta, IL-2, IL-2 receptor alpha subunit, IL-3 receptor, IL-4, IL-6, IL-7, IL-8, IL-12, IL-15, IL-12 gene, IL-17, Interleukin 13 receptor alpha 2, Interleukin-29 ligand, interleukin-1 receptor-associated kinase 4 (IRAK4), Insulin-like growth factor (such as 1, 2), insulin receptor, Integrin alpha-V/beta-3, Integrin alpha-V/beta-5, Integrin alpha-V/beta-6, Integrin alpha-5/beta-1, Integrin alpha-4/beta-1, integrin alpha-4/beta-7, Interferon inducible protein absent in melanoma 2 (AIM2), interferon (such as alpha, alpha 2, beta, gamma), interferon type I receptor, isocitrate dehydrogenase (such as IDH1, IDH2), Janus kinase (JAK, such as JAK1, JAK2), Jun N terminal kinase, Kinase insert domain receptor (KDR), Killer cell Ig like receptor, Kisspeptin (KISS-1) receptor, v-kit Hardy-Zuckerman 4 feline sarcoma viral oncogene homolog (KIT) tyrosine kinase, KIT gene, Kinesin-like protein KIF11, kallikrein-related peptidase 3 (KLK3) gene, Kirsten rat sarcoma viral oncogene homolog (KRAS) gene, lactoferrin, lymphocyte activation gene 3 protein (LAG-3), lysosomal-associated membrane protein family (LAMP) gene, Lanosterol-14 demethylase, LDL receptor related protein-1, Leukotriene A4 hydrolase, Listeriolysin, L-Selectin, Luteinizing hormone receptor, Lyase, Lymphocyte antigen 75, lysine demethylases (such as KDM1, KDM2, KDM4, KDM5, KDM6, A/B/C/D), Lymphocyte function antigen-3 receptor, lymphocyte-specific protein tyrosine kinase (LCK), Lymphotactin, Lyn (Lck/Yes novel) tyrosine kinase, Lysophosphatidate-1 receptor, lysyl oxidase protein (LOX), lysyl oxidase-like protein (LOXL, such as LOXL2), Lysyl oxidase homolog 2, Macrophage migration inhibitory fact, melanoma antigen family A3 (MAGEA3) gene, MAGEC1 gene, MAGEC2 gene, Major vault protein, myristoylated alanine-rich protein kinase C substrate (MARCKS) protein, Melan-A (MART-1) melanoma antigen, Mas-related G-protein coupled receptor, matrix metalloprotease (MMP, such as MMP2, MMP9), myeloid cell leukemia 1 (MCL1) gene, Mcl-1 differentiation protein, macrophage colony-stimulating factor (MCSF) ligand, Melanoma associated antigen (such as 1, 2, 3, 6), melanocyte stimulating hormone ligand, Melanocyte protein Pmel 17, Membrane copper amine oxidase, Mesothelin, Metabotropic glutamate receptor 1, mitogen-activated protein kinase (MEK, such as MEK1, MEK2), Hepatocyte growth factor receptor (MET) gene, MET tyrosine kinase, methionine aminopeptidase-2, mitogen-activate protein kinase (MAPK), Mdm2 p53-binding protein, Mdm4 protein, Metalloreductase STEAPI (six transmembrane epithelial antigen of the prostate 1), Metastin, Methyltransferase, Mitochondrial 3 ketoacyl CoA thiolase, MAPK-activated protein kinase (such as MK2), mTOR (mechanistic target of rapamycin (serine/threonine kinase), mTOR complex (such as 1, 2), mucin (such as 1, 5A, 16), mut T homolog (MTH, such as MTH1), Myc proto-oncogene protein, NAD ADP ribosyltransferase, natriuretic peptide receptor C, Neural cell adhesion molecule 1, Neurokinin receptor, Neuropilin 2, Nitric oxide synthase, Nuclear Factor (NF) kappa B, NF kappa B activating protein, Neurokinin 1 (NK1) receptor, NK cell receptor, NK3 receptor, NKG2 A B activating NK receptor, NIMA-related kinase 9 (NEK9), Noradrenaline transporter, Notch (such as Notch-2 receptor, Notch-3 receptor), nucleophosmin-anaplastic lymphoma kinase (NPM-ALK), 2,5-oligoadenylate synthetase, Nuclear erythroid 2-related factor 2, Nucleolin, Nucleophosmin, O-methylguanine DNA methyltransferase, Ornithine decarboxylase, Orotate phosphoribosyltransferase, orphan nuclear hormone receptor NR4A1, Opioid receptor (such as delta), Osteocalcin, Osteoclast differentiation factor, Osteopontin, OX-40 (tumor necrosis factor receptor superfamily member 4 TNFRSF4, or CD134) receptor, 2 oxoglutarate dehydrogenase, purinergic receptor P2X ligand gated ion channel 7 (P2X7), Parathyroid hormone ligand, p53 tumor suppressor protein, P3 protein, Programmed cell death 1 (PD-1), Proto-oncogene serine/threonine-protein kinase (PIM, such as PIM-1, PIM-2, PIM-3), Poly ADP ribose polymerase (PARP, such as PARP1, 2 and 3), $p^{38}$ kinase, p38 MAP kinase, platelet-derived growth factor (PDGF, such as alpha, beta), P-Glycoprotein (such as 1), Platelet-derived growth factor (PDGF, such as alpha, beta), PKN3 gene, P-Selectin, phosphatidylinositol 3-kinase (PI3K), phosphoinositide-3 kinase (PI3K such as alpha, delta, gamma), phosphorylase kinase (PK), placenta growth factor, Pleiotropic drug resistance transporter, Plexin B1, Polo-like kinase 1, peroxisome proliferator-activated receptors (PPAR, such as alpha, delta, gamma), Preferentially expressed antigen in melanoma (PRAME) gene, Probable transcription factor PML, Programmed cell death ligand 1 inhibitor (PD-L1), Progesterone receptor, prostate specific antigen, Prostatic acid phosphatase, Prostanoid receptor (EP4), proteasome, Protein farnesyltransferase, protein kinase (PK, such as A, B, C), Protein E7, protein tyrosine kinase, protein tyrosine phosphatase beta, polo-like kinase (PLK), PLK1 gene, Prenyl-binding protein (PrPB), protoporphyrinogen oxidase, Prosaposin (PSAP) gene, phosphatase and tensin homolog (PTEN), Purine nucleoside phosphorylase, Pyruvate kinase (PYK), Pyruvate dehydrogenase (PDH), Pyruvate dehydrogenase kinase, Raf protein kinase (such as 1, B), RAF1 gene, Ras GTPase, Ras gene, 5-Alpha-reductase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, RosI tyrosine kinase, Runt-related transcription factor 3, 5100 calcium binding protein A9, Sarco endoplasmic calcium ATPase, Gamma-secretase, Secreted frizzled related protein-2, Semaphorin-4D, SL cytokine ligand, Serine protease, Signaling lymphocytic activation molecule (SLAM) family member 7, spleen tyrosine kinase (SYK), Src tyrosine kinase, tumor progression locus 2 (TPL2), serine/threonine kinase (STK), signal transduction and transcription (STAT, such as STAT-1, STAT-3, STAT-5), Second mitochondria-derived activator of caspases (SMAC) protein, smoothened (SMO) receptor, Sodium phosphate cotransporter 2B, Sodium iodide cotransporter, Somatostatin receptor (such as 1, 2, 3, 4, 5), Sonic hedgehog protein, Specific protein 1 (Sp1) transcription factor, Sphingomyelin synthase, Sphingosine-1-phosphate receptor-1, Sphingosine kinase (such as 1, 2), SRC gene, STAT3 gene, six-transmembrane epithelial antigen of the prostate (STEAP) gene, Steroid sulfatase, stimulator of interferon genes protein, Stimulator of interferon genes (STING) receptor, Stromal cell-derived factor 1 ligand, SUMO (small ubiquitin-like modifier), Superoxide dismutase, Survivin protein, Synapsin 3, Syndecan-1, Synuclein alpha, serine/threonine-protein kinase (TBK, such as TBK1), TATA box-binding protein-associated factor RNA polymerase I subunit B (TAF1B) gene, T-cell surface glycoprotein CD8, T-cell CD3 glycoprotein zeta chain, T-cell differentiation antigen CD6, T cell surface glycoprotein CD28, Tec protein tyrosine kinase, Tek tyrosine kinase receptor, telomerase, Tenascin, Telomerase reverse transcriptase (TERT) gene, Transforming growth factor (TGF, such as beta) kinase, TGF beta 2 ligand, T-cell immunoglobulin and mucin-domain containing-3 (TIM-3), Tissue factor, Tumor necrosis factor (TNF, such as alpha, beta), TNF related apoptosis inducing ligand, TNFR1 associated death domain protein, TNFSF9 gene, TNFSF11 gene, trophoblast glycoprotein (TPBG) gene, Transferrin, Tropomyosin receptor kinase (Trk) receptor (such as TrkA, TrkB, TrkC), Trophoblast glycoprotein, Thymidylate synthase, Tyrosine kinase with immunoglobulin-like and EGF-like domains (TIE) receptor, Toll-like receptor (TLR such as 1-13), topoisomerase (such as I, II, III), Tumor protein 53 (TP53) gene, Transcription factor, Transferase, Transforming growth factor TGF-.beta. receptor kinase, Transglutaminase, Translocation associated protein, Transmembrane glycoprotein NMB, Tumor necrosis factor 13C receptor, Thymidine kinase, Thymidine phosphorylase, Thymidylate synthase, Thymosin (such as alpha 1), Thyroid hormone receptor, Trop-2 calcium signal transducer, Thyroid stimulating hormone receptor, Tryptophan 5-hydroxylase, Tyrosinase, tyrosine kinase (TK), Tyrosine kinase receptor, Tyrosine protein kinase ABL1 inhibitor, tank-binding kinase (TBK), Thrombopoietin receptor, TNF-related apoptosis-inducing ligand (TRAIL) receptor, Tubulin, Tumor suppressor candidate 2 (TUSC2) gene, Tyrosine hydroxylase, Ubiquitin-conjugating enzyme E2I (UBE2I, UBC9), Ubiquitin, Ubiquitin carboxyl hydrolase isozyme L5, Ubiquitin thioesterase-14, Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor protein, Wilms' tumor antigen 1, X-linked inhibitor of apoptosis protein, Zinc finger protein transcription factor or any combination thereof.

The anticancer agent includes agents defined by their mechanism of action or class, including: anti-metabolites/anti-cancer agents such as pyrimidine analogs floxuridine, capecitabine, cytarabine, CPX-351 (liposomal cytarabine, daunorubicin), TAS-118; purine analogs, folate antagonists (such as pralatrexate), and related inhibitors; antiproliferative/antimitotic agents including natural products such as *vinca* alkaloid (vinblastine, vincristine) and microtubule such as taxane (paclitaxel, docetaxel), vinblastin, nocodazole, epothilones, vinorelbine) (NAVELBINE), and epipodophyllotoxins (etoposide, teniposide); DNA damaging agents such as actinomycin, amsacrine, busulfan, carboplatin, chlorambucil, cisplatin, cyclophosphamide) (CYTOXAN), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide; DNA-hypomethylating agent such as guadecitabine (SGI-110) antibiotics such as dactinomycin, daunorubicin, doxorubicin, idarubicin, anthracyclines, mitoxantrone, bleomycins, plicamycin (mithramycin), and; enzymes such as L-asparaginase which systemically metabolizes L-asparagine and deprives cells which do not have the capacity to synthesize their own asparagine; anti-platelet agents; a DNAi oligonucleotide targeting Bcl-2 such as PNT2258; agents that activate or reactivate latent human immunodeficiency virus (HIV) such as panobinostat or romidepsin asparaginase stimulators, such as crisantaspase (ERWINASE®) and GRASPA (ERY-001, ERY-ASP); pan-Trk, ROS1 and ALK inhibitors such as entrectinib anaplastic lymphoma kinase (ALK) inhibitors such as alectinib anti-proliferative/antimitotic alkylating agents such as nitrogen mustards cyclophosphamide and analogs (melphalan, chlorambucil, hexamethylmelamine, and thiotepa), alkyl nitrosoureas (carmustine) and analogs, streptozocin, and triazenes (dacarbazine); antiproliferative/antimitotic antimetabolites such as folic acid analogs (methotrexate); platinum coordination complexes (cisplatin, oxiloplatinim, and carboplatin), procarbazine, hydroxyurea, mitotane, and aminoglutethimide; hormones, hormone analogs (estrogen, tamoxifen, goserelin, bicalutamide, and nilutamide), and aromatase inhibitors (letrozole and anastrozole); anticoagulants such as heparin, synthetic heparin salts, and other inhibitors of thrombin; fibrinolytic agents such as tissue plasminogen activator, streptokinase, urokinase, aspirin, dipyridamole, ticlopidine, and clopidogrel; antimigratory agents; antisecretory agents (breveldin); immunosuppressives tacrolimus, sirolimus, azathioprine, and mycophenolate; compounds (TNP-470, genistein) and growth factor inhibitors (vascular endothelial growth factor inhibitors, and fibroblast growth factor inhibitors such as FPA14; angiotensin receptor blockers, nitric oxide donors; antisense oligonucleotides, such as AEG35156; DNA interference oligonucleotides, such as PNT2258, AZD-9150 antibodies such as trastuzumab and rituximab; anti-HER3 antibodies, such as LJM716 anti-HER2 antibodies such as margetuximab; anti-HLA-DR antibodies such as IMMU-114; anti-IL-3 antibodies, such as JNJ-56022473; anti-OX40 antibodies such as MEDI6469 anti-EphA3 antibodies, such as KB-004; an anti-CD20 antibody such as obinutuzumab; an anti-programmed cell death protein 1 (anti-PD-1) antibody such as nivolumab (OPDIVO, BMS-936558, MDX-1106), pembrolizumab (KEYTRUDA, MK-3477, SCH-900475, lambrolizumab, CAS Reg. No. 1374853-91-4), pidilizumab, and anti-programmed death-ligand 1 (anti-PD-L1) antibodies such as BMS-936559, atezolizumab (MPDL3280A), durvalumab (MEDI4736), avelumab (MSB0010718C), and MDX1105-01, CXCR4 antagonists such as BL-8040; CXCR2 antagonist such as AZD-5069; GM-CSF antibodies such as lenzilumab. Selective estrogen receptor downregulator (SERD) such as fulvestrant (Faslodex); a transforming growth factor-beta (TGF-beta) kinase antagonist such as galunisertib; a bispecific antibody such as MM-141 (IGF-1/ErbB3), MM-111 (Erb2/Erb3), JNJ-64052781 (CD19/CD3). Mutant selective EGFR inhibitors, such as PF-06747775, EGF816, ASP8273, ACEA-0010, BI-1482694. Alpha-ketoglutarate dehydrogenase (KGDH) inhibitors such as CPI-613, XPO1 inhibitors such as selinexor (KPT-330). Isocitrate dehydrogenase 2 (IDH2) inhibitors such as enasidenib (AG-221), and IDH1 inhibitors such as AG-120, and AG-881 (IDH1 and IDH2). Agents that target the interleukin-3 receptor (IL-3R) such as SL-401. Arginine deiminase stimulators, such as pegargiminase (ADI-PEG-20) antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, anti-claudin-18.2 antibodies such as IMAB362.beta.-catenin inhibitors, such as CWP-291 a CD73 antagonist such as MEDI-9447; c-PIM inhibitors, such as PIM447, a BRAF inhibitor such as dabrafenib, vemurafenib, a sphingosine kinase-2 (SK2) inhibitor such as Yeliva. (ABC294640) cell cycle inhibitors such as selumetinib (MEK1/2), sapacitabine, AKT inhibitors such as MK-2206, ipatasertib, afuresertib, anti-CTLA-4 (cytotoxic T-lymphocyte protein-4) inhibitor such as tremelimumab, c-MET inhibitors, such as AMG-337, savolitinib, tivantinib (ARQ-197), capmatinib, tepotinib inhibitors of CSFIR/KIT and FLT3 such as PLX3397, a kinase inhibitor such as vandetanib; E selectin antagonists such as GMI-1271, differentiation inducers such as tretinoin; epidermal growth factor receptor (EGFR) inhibitors such as osimertinib (AZD-9291) topoisomerase inhibitors (doxorubicin, daunorubicin, dactinomycin, eniposide, epirubicin, etoposide, idarubicin, irinotecan, mitoxantrone, pixantrone, sobuzoxane, topotecan, and irinotecan, MM-398 (liposomal irinotecan), vosaroxin and corticosteroids (cortisone, dexamethasone, hydrocortisone, methylprednisolone, prednisone, and prednisolone); growth factor signal transduction kinase inhibitors; dysfunction inducers; nucleoside analogs such as DFP-10917 Axl inhibitors such as BGB-324; BET inhibitors such as INCB-054329, PARP inhibitors such as olaparib, rucaparib, veliparib, Proteasome inhibitors such as ixazomib, carfilzomib (Kyprolis); Glutaminase inhibitors such as CB-839; vaccines such as peptide vaccine TG-01 (RAS), bacterial vector vaccines such as CRS-207/GVAX, autologous Gp96 vaccine, dendritic cells vaccines, Oncoquest-L vaccine, DPX-Survivac, ProstAtak, DCVAC, ADXS31-142, demcizumab (anti-DLL4, Delta-like ligand 4, Notch pathway), napabucasin (BBI-608) smoothened (SMO) receptor inhibitors, such as Odomzo®. (sonidegib, formerly LDE-225), LEQ506, vismodegib (GDC-0449), BMS-833923, glasdegib (PF-04449913), LY2940680, and itraconazole; interferon alpha ligand modulators, such as interferon alfa-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus) (Inmutag, Inter 2A), interferon alfa-2b follow-on biologic (Biosidus-Bioferon, Citopheron, Ganapar) (Beijing Kawin Technology-Kaferon) (AXXO-interferon alfa-2b), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-nl (Humoferon, SM-10500, Sumiferon); interferon gamma ligand modulators, such as interferon gamma (OH-6000, Ogamma 100); IL-6 receptor modulators, such as tocilizumab, siltuximab, AS-101 (CB-06-02, IVX-Q-101); Telomerase modulators, such as tertomotide (GV-1001, HR-2802, Riavax) and imetelstat (GRN-163, JNJ-63935937) DNA methyltransferases inhibitors, such as temozolomide (CCRG-81045), decitabine, guadecitabine (S-110, SGI-110), KRX-0402, and azacitidine; DNA gyrase inhibitors, such as pixantrone and sobuzoxane; Bcl-2 family protein inhibitor ABT-263, venetoclax (ABT-199), ABT-737, and AT-101; Notch inhibitors such as LY3039478, tarextumab (anti-Notch2/3), BMS-906024 anti-myostatin inhibitors such as landogrozumab, hyaluronidase stimulators such as PEGPH-20, Wnt pathway inhibitors such as SM-04755, PRI-724, gamma-secretase inhibitors such as PF-03084014, IDO inhibitors such as indoximod, Grb-2 (growth factor receptor bound protein-2) inhibitor BP1001 (liposomal Grb-2), TRAIL pathway-inducing compounds, such as ONC201, Focal adhesion kinase inhibitors such as VS-4718, defactinib, hedgehog inhibitors such as saridegib, sonidegib (LDE225), glasdegib and vismodegib, Aurora kinase inhibitors such as alisertib (MLN-8237), modulators of HSPB1 activity (heat shock protein 27, HSP27), such as brivudine, apatorsen, ATR inhibitor such as AZD6738, and VX-970, mTOR inhibitors, such as sapanisertib, Hsp90 inhibitors such as AUY922. Murine double minute (mdm2) oncogene inhibitors such as DS-3032b CD137 agonist such as urelumab, Anti-KIR monoclonal antibodies such as lirilumab (IPH-2102). Antigen CD19 inhibitors such as MOR208, MEDI-551, AFM-11, CD44 binders such as A6, CYP17 inhibitors, such as VT-464, ASN-001, ODM-204. RXR agonists such as IRX4204, TLRs (Toll-like receptors) agonists such as IMO-8400 A hedgehog/smoothened (hh/Smo) antagonist such as taladegib. Immunomodulators such as complement C3 modulators, such as Imprime PGG. Intratumural immune-oncology agents such as G100 (TLR4 agonist) IL-15 agonists such as ALT-803 EZH2 (enhancer of zeste homolog 2) inhibitors such as tazemetostat. Oncolytic viruses, such as pelareorep, and talimogene laherparepvec). DOT1L (histone methyltransferase) inhibitors such as pinometostat (EPZ-5676), toxins such as Cholera toxin, ricin, *Pseudomonas* exotoxin, *Bordetella pertussis* adenylate cyclase toxin, diphtheria toxin, and caspase activators; and chromatin. DNA plasmid such as BC-819. PLK inhibitors of PLK 1, 2, and 3, such as volasertib (PLK1). Apoptosis Signal-Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences). Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-pur-in-8 (9H)-one, acalabrutinib (ACP-196), BGB-3111, HM71224, ibrutinib, M-2951, ONO-4059, PRN-1008, spebrutinib (CC-292), TAK-020. Cyclin-dependent Kinase (CDK) Inhibitors: CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02. Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations). Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), vorinostat. Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019. Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics). Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555) and those described in WO 2012/027721 (Gilead Biologics). Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib. Phosphatidylinositol 3-kinase (PI3K) Inhibitors: PI3K inhibitors include inhibitors of PI3K.gamma., PI3K.delta., PI3.beta., PI3K.alpha., and/or pan-PI3K. Examples of PI3K inhibitors include, but are not limited to, ACP-319, AEZA-129, AMG-319, AS252424, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (ZYDELIG®), IPI-145, IPI-443, KAR4141, LY294002, Ly-3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences). Spleen Tyrosine Kinase (SYK) Inhibitors: Examples of SYK inhibitors include, but are not limited to, 6-(1H-indazol-6-yl)-N-(4-morpholinophenyl)imidazo[1,2-alpyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.) and those described in U.S. 2015/0175616. Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, bosutinib, brigatinib, cabozantinib, crenolanib, dacomitinib, dasatinib, dovitinib, E-6201, erlotinib, gefitinib, gilteritinib (ASP-2215), HM61713, icotinib, imatinib, KX2-391 (Src), lapatinib, lestaurtinib, midostaurin, nintedanib, osimertinib (AZD-9291), ponatinib, poziotinib, quizartinib, radotinib, rociletinib, sunitinib, and TH-4000. Further anticancer agents include: alkylating agents such as thiotepa and cyclophosphamide (CYTOXAN); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlomaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel) (TAXOL), abraxane, docetaxel) (TAXOTERE), cabazitaxel, BIND-014; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2', 2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine) (GEMZAR®); 6-thioguanine; mercaptopurine; methotrexate; vinblastine; platinum; etoposide (VP-16); ifosfamide; mitroxantrone; vancristine; vinorelbine) (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; FOLFIRI (fluorouracil, leucovorin, and irinotecan); and pharmaceutically acceptable salts, acids, or derivatives of any of the above.

Also included in the definition of anticancer agents are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors. Examples of anti-estrogens and SERMs include, for example, tamoxifen (including NOLVADEX), raloxifene, droloxifene, 4-hydroxytamoxifen, trioxifene, keoxifene, LY117018, onapristone, and toremifene) (FARESTON). Inhibitors of the enzyme aromatase regulate estrogen production in the adrenal glands. Examples include 4(5)-imidazoles, aminoglutethimide, megestrol acetate) (MEGACE), exemestane, formestane, fadrozole, vorozole) (RIVISOR), letrozole) (FEMARA), and anastrozole) (ARIMIDEX). Examples of anti-androgens include apalutamide, abiraterone, enzalutamide, flutamide, galeterone, nilutamide, bicalutamide, leuprolide, goserelin, ODM-201, APC-100, ODM-204. Examples of progesterone receptor antagonist include onapristone.

Anti-angiogenic agents include, but are not limited to, retinoid acid and derivatives thereof, 2-methoxyestradiol, ANGIOSTATIN, ENDOSTATIN, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, .alpha., .alpha.'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethyl-amine, 2-chloroethylamine, 2-trifluoroethylamine, 3-bromopropylamine, and p-halobenzylamines; and selenohomocysteine lactone. Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethy)dithio)butanoic acid, p-2-amino-3-methyl-3-((2-aminoethy)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

The API can be an immunotherapeutic agent. Immunotherapeutic agents include, and are not limited to, therapeutic antibodies suitable for treating patients. Some examples of therapeutic antibodies include simtuzumab, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, dinutuximab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, pasudotox, narnatumab, naptumomab, necitumumab, nimotuzumab, nofetumomab, obinutuzumab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, ramucirumab (CYRAMZA®) rilotumumab, rituximab, robatumumab, samalizumab, satumomab, sibrotuzumab, siltuximab, solitomab, tacatuzumab, taplitumomab, tenatumomab, teprotumumab, tigatuzumab, tositumomab, trastuzumab, ABP-980, tucotuzumab, ubilituximab, veltuzumab, vorsetuzumab, votumumab, zalutumumab, CC49, OBI-833 and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

The composition comprises, in place of an API or in addition thereto, a targeting moiety, such as a peptide or protein ligand or domain, covalently attached to the surface of the microparticles or nanoparticles, which targeting moiety specifically or preferentially binds to a target site (such as a cell surface receptor or binding partner for the targeting moiety), such that the micro- or nanoparticle bearing such a targeting moiety will be specifically or preferentially directed to the target site in vivo. The targeting moiety bearing micro- or nanoparticle may further comprise an API that is encapsulated or embedded within the micro- or nanoparticle that can be released or otherwise effective at the target site. In fact, sialic acid can itself be a targeting moiety for cancer cells.

By having targeting moieties, target specific nanoparticles are able to efficiently bind toor otherwise associate with a biological entity, for example, a membrane component or cell surface receptor. Targeting of a therapeutic agent (e.g., to a particular tissue or cell type, to a specific diseased tissue but not to normal tissue, etc.) is desirable for the treatment of tissue specific diseases such as cancer (e.g., prostate cancer). For example, in contrast to systemic delivery of a cytotoxic anti-cancer agent, targeted delivery could prevent the agent from killing healthy cells.

Additionally, targeted delivery would allow for the administration of a lower dose of the agent, which could reduce the undesirable side effects commonly associated with traditional chemotherapy. As discussed above, the target specificity of the nanoparticles of the invention will be maximized by optimizing the ligand density on the nanoparticle. Targeting moieties can be covalently bound to the surface of the nanoparticle or microparticle. For example, targeting moieties can be covalently bound to the anionic polymer (e.g., by coupling one or more carboxylic acid or other function group moieties), the PLGA/PLA (e.g., via a polymer terminal) or by incorporating yet another molecule or polymer into the interpenetrating network. For example, the targeting moiety can be covalently linked to a polyethylene glycol (PEG) molecule or PLGA-PEG diblock and added to the emulsion with the anionic polymer.

For example, a targeting moiety can be a moiety able to bind to or otherwise associate with a biological entity, for example, a membrane component, a cell surface receptor, prostate specific membrane antigen, or the like. In the case of the instant invention, the targeting moiety is a low-molecular weight PSMA ligand. The term “bind” or “binding,” as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions.

“Biological binding” defines a type of interaction that occurs between pairs of molecules including proteins, nucleic acids, glycoproteins, carbohydrates, hormones, or the like.

The term “binding partner” refers to a molecule that can undergo binding with a particular molecule. “Specific binding” refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

In preferred embodiments, the targeting moiety of the invention is a small molecule. In certain embodiments, the term “small molecule” refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol.

In particularly preferred embodiments, the small molecule targeting moiety targets prostate cancer tumors, and, in particular, the small molecule targeting moiety is a PSMA peptidase inhibitor. These moieties are also referred to herein as "low-molecular weight PSMA ligands." When compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al. 1997, Clin. Cancer Res., 3:81), as described in US Patent Publication 2014/0235706.

In some embodiments, small molecule targeting moieties that may be used to target cells associated with prostate cancer tumors include PSMA peptidase inhibitors such as 2-PMPA, GPI5232, VA-033, phenylalkylphosphonamidates (Jackson et al., 2001, Curr. Med. Chem., 8:949; Bennett et al, 1998, J. Am. Chem. Soc., 120:12139; Jackson et al., 2001, J. Med. Chem., 44:4170; Tsulcarnoto et al., 2002, Bioorg. Med. Chem. Lett., 12:2189; Tang et al., 2003, Biochem. Biophys. Res. Commun., 307:8; Oliver et al., 2003, Bioorg. Med. Chem., 11:4455; and Maung et al., 2004, Bioorg. Med. Chem., 12:4969), and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives (Majer et al., 2003, J. Med. Chem., 46:1989; and U.S. Patent Publication 2005/0080128). In some embodiments, small molecule targeting moieties that may be used to target cells associated with prostate cancer tumors include hydroxamate derivatives (Stoermer et al., 2003, Bioorg. Med. Chem. Lett., 13:2097). In some embodiments, small molecule targeting moieties that may be used to target cells associated with prostate cancer tumors include PBDA- and urea-based inhibitors, such as ZJ 43, ZJ 11, ZJ 17, ZJ 38 (Nan et al. 2000, J. Med. Chem., 43:772; and Kozikowski et al., 2004, J. Med. Chem., 47:1729), and/or and analogs and derivatives thereof. In some embodiments, small molecule targeting moieties that may be used to target cells associated with prostate cancer tumors include putrescine, spermine, and spermidine, androgen receptor targeting agents (ARTAs), such as those described in U.S. Pat. Nos. 7,026,500; 7,022,870; 6,998,500; 6,995,284; 6,838,484; 6,569,896; 6,492,554; and in U.S. Patent Publications 2006/0287547; 2006/0276540; 2006/0258628; 2006/0241180; 2006/0183931; 2006/0035966; 2006/0009529; 2006/0004042; 2005/0033074; 2004/0260108; 2004/0260092; 2004/0167103; 2004/0147550; 2004/0147489; 2004/0087810; 2004/0067979; 2004/0052727; 2004/0029913; 2004/0014975; 2003/0232792; 2003/0232013; 2003/0225040; 2003/0162761; 2004/0087810; 2003/0022868; 2002/0173495; 2002/0099096; 2002/0099036. A related aspect of the invention provides a pharmaceutical composition comprising the subject composition, and a pharmaceutically accepted carrier or excipient. Pharmaceutical compositions are described below in more details in a separate section.

The current invention also provides a vehicle for the delivery of nucleic acid to enhance the in vitro and in vivo cell uptake and transfection. Examples of nucleic acid includes DNA, RNA, PNA, siRNA, microRNA, antisense, etc.

Production of the Particles

The invention described herein provides several basic methods for the preparation of particles that present sialic acid residues on their surfaces.

The particles can be manufactured from the coprecipitation or coacervation of a hydrophobic and/or neutral biocompatible polymer, such as PLGA or PLA, and the polysialic acid. Without being bound by any theory, it is believed that the polymer backbones intertwine or interlace while in the organic phase of emulsion.

As used herein, "small (amount)" refers to a relatively small amount/volume of the first solution of the second solvent as compared to the volume of the first solvent with PLGA polymer, such that emulsification of the first solution of the second solvent in the polymer solution in the first solvent forms an emulsion (i.e., the first emulsion) with the continuous phase being the polymer solution. Typically, the volume ratio between the small amount of the first solution of the second solvent, and the first solvent, is at least about 1:n, wherein n can be 1, 2, 3, 4, 5, 6, 7, 8, 9, 10, 20, 30, 40, 50, 60, 70, 80, 90, or 100.

As used herein, "large (amount)" refers to the relatively large amount/volume of the second solution of the second solvent as compared to the volume of the first emulsion, such that emulsification of the first emulsion in the second solution of the second solvent forms an emulsion (i.e., the second emulsion) with the continuous phase being the second solution of the second solvent. Typically, the volume ratio between the first emulsion and the large amount of the second solution of the second solvent, is at least about 1:m, wherein m can be 1, 2, 3, 4, 5, 6, 7, 8, 9, 10, 20, 30, 40, 50, 60, 70, 80, 90, or 100.

Using the methods of preparation described herein, the polysialic acid is tightly integrated into the produced microparticles or nanoparticles.

The incorporation of the polysialic acid into the microparticles or nanoparticles can be stable and tight. Thus, preferably, the method further comprises washing said microparticles or nanoparticles, and/or concentrating said microparticles or nanoparticles to a desired volume.

An emulsion process may be used to prepare the particles described herein. The invention includes a method for the preparation of microparticles or nanoparticles presenting sialic acid moieties on their surfaces comprising: (1) dissolving a biodegradable polymer (and optionally an active agent, such as a pharmaceutical ingredient (API), or a poorly water-soluble compound) in a first solvent to form a polymer solution; (2) emulsifying the polymer solution in a solution of a second solvent to form an emulsion, wherein the first solvent is not miscible or partially miscible with the second solvent, and wherein the solution of the second solvent comprises a polysialic acid, said solution of the second solvent optionally further comprising a surfactant and/or an API soluble in the second solvent; and (3) removing the first solvent to form said microparticles or nanoparticles having the surface sialic acid moieties.

The invention also provides a double-emulsification method for the preparation of microparticles or nanoparticles having surface sialic acid moieties, said method comprising: (1) dissolving a biodegradable polymer (and optionally an active agent, an API, or a poorly water soluble compound) in a first solvent to form a polymer solution; (2) adding a second solvent to the polymer solution to form a mixture, wherein the first solvent is not miscible or partially miscible with the second solvent, and wherein the first solution of the second solvent optionally comprises an active agent which may be the same or different from the API dissolved in the first solvent; (3) emulsifying the mixture to form a first emulsion; (4) emulsifying the first emulsion in a second solution of the second solvent to form a second emulsion, wherein the second solution of the second solvent comprises a polysialic acid, and optionally further comprises a surfactant; and (5) removing the first solvent to form microparticles or nanoparticles having surface sialic acid moiety.

The API in the current invention can be a nucleic acid therapeutic agent. Exemplary nucleic acid therapeutic agents include, but are not limited to, those approved by the FDA, subject to a new drug application with the FDA, in clinical trials or in preclinical research. The nucleic acid molecules include molecules that encode therapeutic proteins, antigenic molecules, and inhibitory molecules. For example, nucleic acid molecules capable of mediating RNA interference include molecules active in RNA interference (RNAi molecules), including a duplex RNA such as antisense, ribozymes, an siRNA (small interfering RNA), miRNA (micro RNA), shRNA (short hairpin RNA), shortmers, antagomirs, mRNA, tRNA, ddRNA (DNA-directed RNA), piRNA (Piwi-interacting RNA), or rasiRNA (repeat associated siRNA), and modified forms thereof. The molecules can also include DNAs, plasmids, vectors, hybrid oligonucleotides, catalytic DNA, or aptamers.

Coding Nucleic acids and polynucleotides can include a region encoding a polypeptide of interest (e.g., a coding region), a 5'-terminus of the first region (e.g., a 5'-UTR), a 3'-terminus of the first region (e.g., a 3'-UTR), at least one 5'-cap region, and/or a 3'-stabilizing region. A nucleic acid can include a poly-A region or a Kozak sequence (e.g., in the 5'-UTR), one or more intronic nucleotide sequences capable of being excised from the polynucleotide, a 5' cap structure, a chain terminating nucleotide, a stem loop, a polyA sequence, and/or a polyadenylation signal. A nucleic acid may include one or more alternative components (e.g., an alternative nucleoside). For example, the 3'-stabilizing region may contain an alternative nucleoside such as an L-nucleoside, an inverted thymidine, or a 2'-O-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methyl-pseudouridine or 1-ethyl-pseudouridine), a 5-substituted cytidine (e.g., 5-methyl-cytidine) and/or carnosine and anserine.

The length of the polynucleotide sequence that is sufficient to encode for a dipeptide or more, such as a tripeptide, tetrapeptide, pentapeptide, hexapeptide, heptapeptide, octapeptide, nonapeptide or decapeptide. In some cases, a polynucleotide is greater than 30 nucleotides in length, such as greater than 35 nucleotides, at least 40 nucleotides, at least 45 nucleotides, at least 55 nucleotides, at least 60 nucleotides, at least 80 nucleotides, at least 90 nucleotides, at least 100 nucleotides or more.

Nucleic acids and polynucleotides may include one or more naturally occurring components, including any of the canonical nucleotides A (adenosine), G (guanosine), C (cytosine), U (uridine), or T (thymidine). In one embodiment, all or substantially all of the nucleotides comprising (a) the 5'-UTR, (b) the open reading frame (ORF), (c) the 3'-UTR, (d) the poly A tail, and any combination of (a, b, c, or d above) comprise naturally occurring canonical nucleotides A (adenosine), G (guanosine), C (cytosine), U (uridine), or T (thymidine).

Nucleic acids and polynucleotides can include one or more components to increase stability, reduce substantial induction of the innate immune response of a cell into which the polynucleotide is introduced, enhance the efficiency of protein production, intracellular retention of the polynucleotides, viability of contacted cells, and/or reduce immunogenicity.

Polynucleotides and nucleic acids may be naturally or non-naturally occurring. Polynucleotides and nucleic acids may include one or more modified (e.g., altered or alternative) nucleobases, nucleosides, nucleotides, or combinations thereof. The nucleic acids and polynucleotides useful in a nanoparticle composition can include any useful modification or alteration, such as to the nucleobase, the sugar, or the internucleoside linkage (e.g., to a linking phosphate/to a phosphodiester linkage/to the phosphodiester backbone). Alterations (e.g., one or more alterations) are present in each of the nucleobase, the sugar, and the internucleoside linkage. Alterations according to the present disclosure may be alterations of ribonucleic acids (RNAs) to deoxyribonucleic acids (DNAs), e.g., the substitution of the 2'-OH of the ribofuranosyl ring to 2'-H, threose nucleic acids (TNAs), glycol nucleic acids (GNAs), peptide nucleic acids (PNAs), locked nucleic acids (LNAs), or hybrids thereof.

Polynucleotides and nucleic acids may or may not be uniformly altered along the entire length of the molecule. For example, one or more or all types of nucleotide (e.g., purine or pyrimidine, or any one or more or all of A, G, U, C) may or may not be uniformly altered in a polynucleotide or nucleic acid, or in a given predetermined sequence region thereof. In some instances, all nucleotides X in a polynucleotide (or in a given sequence region thereof) are altered, wherein X may any one of nucleotides A, G, U, C, or any one of the combinations A+G, A+U, A+C, G+U, G+C, U+C, A+G+U, A+G+C, G+U+C or A+G+C.

Different sugar alterations and/or internucleoside linkages (e.g., backbone structures) may exist at various positions in a polynucleotide. One of ordinary skill in the art will appreciate that the nucleotide analogs or other alteration(s) may be located at any position(s) of a polynucleotide such that the function of the polynucleotide is not substantially decreased. An alteration may also be a 5'- or 3'-terminal alteration. In some embodiments, the polynucleotide includes an alteration at the 3'-terminus.

In some instances, nucleic acids do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDA5, etc., and/or 3) termination or reduction in protein translation.

The nucleic acids can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors). In some embodiments, the nucleic acids may include one or more messenger RNAs (mRNAs) having one or more alternative nucleoside or nucleotides (i.e., alternative mRNA molecules).

In some embodiments, a cationic complexing agent may be used to complex the nucleic acid cargo before the encapsulation.

Said cationic complexing agent in the current invention may be a nitrogen, sulfur or phosphorus containing molecule such as a small molecule compound, a lipid, a polymer or a dendrimer. The molecule is preferably amphiphilic, having one or more cationic moieties and one or more hydrophobic moieties. Cationic moieties can be nitrogen, sulfur or phosphorus containing groups. Preferred cationic moieties include primary or secondary amines, ammoniums or phosphoniums. The hydrophobic moiety can be an organic or inorganic group. Preferred hydrophobic groups include substituted or unsubstituted, saturated or unsaturated higher alkyls, acyls or esters (C3-C20 or more). The hydrophobic groups can be linear, branched or cyclized (such as aryl groups or cholesterol and analogs thereof).

Small molecule complexing agent used in the present invention is typically a nitrogen, sulfur or phosphorus containing compound or salt thereof. Non-limiting examples of small molecule complexing agents include ethyl lauroyl arginate HCl (LAE), tripropyl amine, tributyl amine, triphenyl amine, hexadecylamine, hexylamine, Didodecyldimethylammonium bromide, Dodecyltrimethylammonium bromide (DTAB), Cetrimonium bromide (CTAB), benzathine, dimethyldioctadecylammonium bromide, benethamine, hydrabamine, stearalkonium chloride, DC-Cholesterol HCl, cetylpyridinium chloride, 1,2-distearoyl-3-dimethylammonium-propane, DODMA, lipofectin, etc.

Lipids that can be used in the present invention as the complexing agent may be cationic lipids or ionizable lipids.

Cationic lipids are amphiphilic molecules that have a cationic head group and a hydrophobic tail group connected by either stable or degradable linkages. Guanidine, imidazole, pyridinium, piperizine, and amino acid (e.g., lysine, arginine, ornithine, and tryptophan) are common head groups used in lipid modification. Lipids that can be used as complexing agent in the present invention include but not limit to monovalent aliphatic lipids with single amine functionality in their head group, e.g., N[1-(2,3-dioleyloxy) propyl]-N,N,N-trimethylammonium chloride (DOTMA)), N-(2-hydroxyethyl)-N,N-dimethyl-2,3-bis(tetradecyloxy-1-propanaminiumbromide) (DMRIE), multivalent aliphatic lipids with several amine functionalities in head group, e.g., spermine groups, e.g., dioctadecylamidoglycylspermine (DOGS), or cationic cholesterol derivatives, e.g., 3b-[N—(N0, N0-dimethylaminoethane) carbamoyl]cholesterol (DC-Chol), bis-guanidium-tren-cholesterol (BGTC), and neutral helper lipids such as 1,2-dioleyl-sn-glycerol-3-phosphoethanolamine (DOPE) or cholesterol, which were added to complex of DNA and RNA and cationic lipids to improve transfection efficiency.

Ionizable lipids are a class of lipid molecules that are neutral and non-ionic at physiological pH but will be protonated to become positively charged at lower pHs. Ionizable lipids can also form the complex with the SA-containing entity while promoting endosome escape and reducing toxicity. Examples of commercially available ionizable lipids include DLin-KC2-DMA, DLin-MC3-DMA, DLin-DMA, DODMA, and DODAP.

In order to increase the stability, functionality and other performance properties of the RNA-lipid complex, other chemical entities commonly used in lipid nanoparticle (LNP) formulations such as structural lipids, PEGylated lipids, cholesterol, phospholipids, etc. may be added to the nanoparticle formulations of the present invention.

Polymeric complexing agents can be cationic polymers comprising one or more cationic monomers and include polylysine, cell-penetrating peptides (such as polyarginine), polyethyleneimine, chitosan, and poly(amino ester).

Polylysine is a cationic homopolypeptide and can be an α-polylysine or F-polylysine. Polylysine contains a positively charged amino group at neutral pH. α-Polylysine is a synthetic polymer and can be in the form of poly-L-lysine (PLL) and poly-D-lysine (PDL), respectively. &-Polylysine (F-poly-L-lysine, EPL) is typically produced as a homopolypeptide of approximately 25-30 L-lysine residues. Polylysine used in the present invention can be a copolymer of lysine and other chemical entity. Polylysine can also be modified to possess specific properties. For example, modified polylysine may be more hydrophobic by, for example, alkylating or acylating an amine group on one or more lysines.

Cell-penetrating peptides (CPPs) have the ability to translocate the plasma membrane and facilitate the delivery of various molecular cargoes to the cytoplasm or an organelle. Some cell-penetrating peptides such as polyarginine are cationic and are suitable as complexing agent for nucleic acids.

Polyethyleneimine (PEI) is a polymer with a repeating unit composed of an amine group and two carbon aliphatic (CH2CH2) spacer. There are linear and branched PEIs. The linear structure facilitates crystallization of the polymer and, as a result, linear PEIs can be crystalline and solid at room temperatures. Branched PEIs can be liquid at room temperatures. Linear PEIs contain primarily secondary amines, in contrast to branched PEIs which contain primary, secondary and tertiary amino groups.

Chitosan is a linear polysaccharide composed of randomly distributed β-(1→4)-linked D-glucosamine (deacetylated unit) and N-acetyl-D-glucosamine. The amino group in chitosan has a pKa value of ~6.5, which leads to significant protonation in neutral solution and a positive charge. Thus, chitosan can be used to form complexes with nucleic acid via ionic interaction.

Preferred poly(amino ester)s are biodegradable and biocompatible polymers. One example of poly(amino ester) is poly[α-(4-aminobutyl)-1-glycolic acid].

Poly(β-amino ester)s (PBAEs) are a class of polymers obtained from di-acrylates and functional amines including a primary and a secondary amine, preferably formed via Michael addition reaction. PBAEs are pH-sensitive, biodegradable and biocompatible. The pH buffering capability of PBAEs, which results from the presence of tertiary amines in the PBAE structure, facilitates endosomal escape and hence intracellular delivery of therapeutics.

The cationic complexing agents can also be modified to render other desired properties. For example, the cationic complexing agents, such as PBAE, can be PEGylated, thereby extending the in vivo circulation time. The cationic complexing agents, particularly polymers, can be optimized for molecule weight, degradation profile, in vivo half-life, pH responsiveness, and other properties that may be desired for specific applications.

Preferably, in the emulsification process, the weight ratio of the PLGA solution to the aqueous solution is typically from 1:1,000 to 10:1, preferable from 1:100 to 1:1.

As used herein, miscibility is defined to be the property of liquids to mix in all proportions, forming a homogeneous solution. Substances/liquids are said to be immiscible or not miscible, if in some proportion, they do not form a solution.

Exemplary solvents miscible with water include acetone, tetrahydrofuran (THF), acetonitrile, dimethyl sulfoxide (DMSO), dimethylformamide (DMF).

The double emulsion process may be particularly useful when an active agent, such as a drug or an active pharmaceutical ingredient (API), such as a protein-based therapeutic prepared in an aqueous solution, is first emulsified with a pharmaceutically acceptable polymer solution to form a first emulsion such that the API is encapsulated within the polymer solution. Then the polymer, and the therapeutics encapsulated therein, is again emulsified in a larger volume of solvent to form a second emulsion (e.g., the water-in-oil-in-water or w/o/w type double emulsion), before the microparticle or nanoparticle is formed.

For example, in the above described w/o/w technique, a relatively small amount of a first solution of the second solvent (e.g., an aqueous protein solution) (e.g., about 20%, 15%, 10%, 5% v/v of the organic solvent) may be introduced into a relatively larger amount of a first solvent (e.g., an organic solvent), such as methylene chloride or ethyl acetate, that dissolves the hydrophobic polymer PLGA. The first emulsion is then formed using a suitable method, e.g., probe sonication or homogenization. After formation of the first emulsion, a second emulsion is formed by introducing the first emulsion into a larger volume of a second solution of the second solvent (e.g., about at least about 2-fold, 3-fold, 4-fold, 5-fold, 6-fold, 10-fold of the first emulsion) containing an emulsifier, e.g., polyvinyl alcohol. Again, a homogenization method can be used to form the second emulsion. This is next followed by a period of solvent evaporation leading to the hardening of the polymer, typically by stirring for some hours. As a result, the protein solution is trapped into the relative hydrophobic matrix of the PLGA polymer forming small inclusions. Finally, the microparticles or nanoparticles formed are collected, washed (e.g., with distilled water) via repeated centrifugation or filtration, followed by dehydration, typically by lyophilization.

In any of the aspects described above, preferably, the first solvent is methylene chloride, ethyl acetate, or chloroform. Preferably, the second solution of the second solvent comprises a surfactant comprising organic or inorganic pharmaceutical excipients; various polymers; oligomers; natural products; nonionic, cationic, zwitterionic, or ionic surfactants; and mixtures thereof. The surfactant may comprise polyvinyl alcohol (PVA), polyvinylpyrrolidone (PVP), a polysorbate (Tween series) surfactant, a PEO-PPO-PEO polyethyleneoxide polypropylene oxide triblock copolymer (Pluronic series or Poloxamer series) surfactant, or a t-octylphenyl-polyethylene glycol (Triton X-100) surfactant or a salt, derivative, copolymer, or mixture thereof. Preferably, the surfactant is PVA (see examples).

Preferably, the emulsifying step comprises homogenization, mechanical stirring, and/or microfluidization.

Preferably, the first solvent is removed through solvent exchange and/or evaporation.

The solvent used in the dissolving step for the polymer can be any type of solvent that dissolves the polymer (e.g., PLGA). However, a volatile solvent is preferably used for its removal. For example, preferred solvents for forming the PLGA solution include methylene chloride, ethyl acetate, and chloroform.

In the emulsifying step, the (aqueous) solution may contain a surfactant or surface stabilizer. Surfactants generally include compounds that lower the surface tension of a liquid, the interfacial tension between two liquids, or that between a liquid and a solid. Surfactants may act as detergents, wetting agents, emulsifiers, foaming agents, and dispersants. Surfactants are usually organic compounds that are amphiphilic, which contain both hydrophobic groups (usually branched, linear, or aromatic hydrocarbon chain(s), fluorocarbon chain(s), or siloxane chain(s) as "tail(s)") and hydrophilic groups (usually heads). Surfactants are most commonly classified according to their polar head group: a non-ionic surfactant has no charge groups in its head; an ionic surfactant carries a net charge—if the charge is negative, the surfactant is anionic, and if the charge is positive, it is cationic. If a surfactant contains a head with two oppositely charged groups, it is termed zwitterionic. Preferably, anionic or zwitterionic surfactants, such as those containing carboxyl groups ("carboxylates"), are preferably used in the instant invention. The carboxylates are the most common surfactants and comprise the alkyl carboxylates, such as sodium stearate, sodium lauroyl sarcosinate, and carboxylate-based fluorosurfactants such as perfluorononanoate, perfluorooctanoate (PFOA or PFO).

While not wishing to be bound by any particular theory, surfactant may be useful for the formation and stabilization of the emulsion droplets. The surfactant may also comprise organic or inorganic pharmaceutical excipients, various polymers, oligomers, natural products, nonionic, cationic, zwitterionic, or ionic surfactants, and mixtures thereof.

The surfactants that can be used for the preparation of the subject (PLGA) microparticles or nanoparticles include polyvinyl alcohol, polyvinylpyrrolidone, Tween series, Pluronic series, Poloxamer series, Triton X-100, etc. Additional suitable surfactants are provided herein below.

The emulsification process may be carried out by any art-recognized means, such as homogenization, ultrasonication, mechanical stirring, microfluidization, or a combination thereof.

The removal of solvent is usually achieved by, for example, solvent exchange and evaporation.

Combinations of more than one surfactant can be used in the invention. Useful surfactants or surface stabilizers which can be employed in the invention may include, but are not limited to, known organic and inorganic pharmaceutical excipients. Such excipients include various polymers, low molecular weight oligomers, natural products, and surfactants. Surfactants or surface stabilizers include nonionic, cationic, zwitterionic, and ionic surfactants.

Representative examples of other useful surfactants or surface stabilizers include hydroxypropyl methylcellulose, hydroxypropylcellulose, polyvinylpyrrolidone, sodium lauryl sulfate, sodium dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available TWEENS® such as e.g., TWEEN 20® and TWEEN 80® (ICI Specialty Chemicals)); polyethylene glycols (e.g., CARBOWAXS 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., PLURONICS F68® and F108®, which are block copolymers of ethylene oxide and propylene oxide); poloxamines (e.g., TETRONIC 908®, also known as POLOXAMINE 908®, which is a tetrafunctional block copolymer derived from sequential addition of propylene oxide and ethylene oxide to ethylenediamine (BASF Wyandotte Corporation, Parsippany, N.J.)); TETRONIC 1508® (T-1508) (BASF Wyandotte Corporation), TRITONS X-200®, which is an alkyl aryl polyether sulfonate (Rohm and Haas); CRODESTAS F-110®, which is a mixture of sucrose stearate and sucrose distearate (Croda Inc.); p-isononylphenoxypoly-(glycidol), also known as OLIN-1OG® or SURFACTANT 10-G® (Olin Chemicals, Stamford, Conn.); Crodestas SL-40 (Croda, Inc.); and SA9OHCO, which is C18H37CH2 (CON(CH3)-CH2(CHOH)4(CH2OH)2 (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, and the like.

Examples of useful cationic surfactants or surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt) (also known as DPPE-PEG(2000)-Amine Na) (Avanti Polar Lipids, Alabaster, A1), Poly(2-methacryloxyethyl trimethylammonium bromide) (Polysciences, Inc., Warrington, Pa.) (also known as S1001), poloxamines such as TETRONIC 908®, also known as POLOXAMINE 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quaternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, C12-15 dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy) ammonium chloride or bromide, N-alkyl (C12-18)dimethylbenzyl ammonium chloride, N-alkyl (C14-18)dimethyl-benzyl ammonium chloride, N-tetradecylidmethylbenzyl ammonium chloride monohydrate, dimethyl didecyl ammonium chloride, N-alkyl and (C12-14) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl(C12-14) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, C12, C15, C17 trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336TM), POLYQUAT 10TM, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surfactants or surface stabilizers and other useful cationic surfactants or surface stabilizers are described in J. Cross and E. Singer, Cationic Surfactants: Analytical and Biological Evaluation (Marcel Dekker, 1994); P. and D. Rubingh (Editor), Cationic Surfactants: Physical Chemistry (Marcel Dekker, 1991); and J. Richmond, Cationic Surfactants: Organic Chemistry, (Marcel Dekker, 1990), each of which is incorporated by reference herein in its entirety.

Nonpolymeric cationic surfactants or surface stabilizers are any nonpolymeric compound, such as benzalkonium chloride, a carbonium compound, a phosphonium compound, an oxonium compound, a halonium compound, a cationic organometallic compound, a quaternary phosphorous compound, a pyridinium compound, an anilinium compound, an ammonium compound, a hydroxylammonium compound, a primary ammonium compound, a secondary ammonium compound, a tertiary ammonium compound, and quaternary ammonium compounds of the formula NR1R2R3R4(+). For compounds of the formula NR1R2R3R4(+): (i) none of R1-R4 are CH3; (ii) one of R1-R4 is CH3; (iii) three of R1-R4 are CH3; (iv) all of R1-R4 are CH3; (v) two of R1-R4 are CH3, one of R1-R4 is C6H5CH2, and one of R1-R4 is an alkyl chain of seven carbon atoms or less; (vi) two of R1-R4 are CH3, one of R1-R4 is C6H5CH2, and one of R1-R4 is an alkyl chain of nineteen carbon atoms or more; (vii) two of R1-R4 are CH3 and one of R1-R4 is the group C6H5 (CH2)n, where n>1; (viii) two of R1-R4 are CH3, one of R1-R4 is C6H5CH2, and one of R1-R4 comprises at least one heteroatom; (ix) two of R1-R4 are CH3, one of R1-R4 is C6H5CH2, and one of R1-R4 comprises at least one halogen; (x) two of R1-R4 are CH3, one of R1-R4 is C6H5CH2, and one of R1-R4 comprises at least one cyclic fragment; (xi) two of R1-R4 are CH3 and one of R1-R4 is a phenyl ring; or (xii) two of R1-R4 are CH3 and two of R1-R4 are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surfactants or surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surfactants or surface stabilizers are commercially available and/or can be prepared by techniques known in the art.

Preferably, the surface of the subject microparticle or nanoparticle is composed of a material that minimizes nonspecific or unwanted biological interactions between the particle surface and the interstitium, e.g., the particle surface may be coated with a material to prevent or decrease non-specific interactions. Steric stabilization by coating particles with hydrophilic layers such as poly(ethylene glycol) (PEG) and its copolymers such as PLURONICS (including copolymers of poly(ethylene glycol)-bl-poly(propylene glycol)-bl-poly(ethylene glycol)) may reduce the non-specific interactions with proteins of the interstitium as demonstrated by improved lymphatic uptake following subcutaneous injections.

As used herein, “small (amount)” refers to a relatively small amount/volume of the first solution of the second solvent as compared to the volume of the first solvent with PLGA polymer, such that emulsification of the first solution of the second solvent in the polymer solution in the first solvent forms an emulsion (i.e., the first emulsion) with the continuous phase being the polymer solution. Typically, the volume ratio between the small amount of the first solution of the second solvent, and the first solvent, is at least about 1:n, wherein n can be 1, 2, 3, 4, 5, 6, 7, 8, 9, 10, 20, 30, 40, 50, 60, 70, 80, 90, or 100.

As used herein, “large (amount)” refers to the relatively large amount/volume of the second solution of the second solvent as compared to the volume of the first emulsion, such that emulsification of the first emulsion in the second solution of the second solvent forms an emulsion (i.e., the second emulsion) with the continuous phase being the second solution of the second solvent. Typically, the volume ratio between the first emulsion and the large amount of the second solution of the second solvent, is at least about 1:m, wherein m can be 1, 2, 3, 4, 5, 6, 7, 8, 9, 10, 20, 30, 40, 50, 60, 70, 80, 90, or 100.

The incorporation of the polysialic acid into the particles can be stable and tight. Thus, preferably, the method further comprises washing said microparticles or nanoparticles, and/or concentrating said microparticles or nanoparticles to a desired volume.

The microparticles and nanoparticles produced using the methods of the invention may routinely undergo washing as part of a purification process that removes impurity, and/or concentrates the microparticles and nanoparticles so produced.

The microparticles and nanoparticles produced using the methods of the invention may also undergo more stringent washing tests, e.g., as part of the quality control process, to ensure that the polysialic acid residues are stably incorporated into the microparticles and nanoparticles so produced.

Preferably, the washing test uses conditions identical to or similar to those exemplified below. Preferably, said polysialic acid is durably attached to the surface of the microparticles and nanoparticles and can sustain multiple washing cycles.

Preferably, the polysialic acid on particle surface can sustain certain washing tests, such as the wash test exemplified herein, without significantly losing the amount of polysialic acid.

Preferably, after washing, the microparticles or nanoparticles retain at least about 50%, 60%, 75%, 80%, 85%, 90%, 95%, or 99% of the amount of sialic acid moiety.

Particle Sizes

The size of the subject microparticles and nanoparticles is from about 1 nm to about 1000 μm, preferably from about 10 nm to about 100 μm, and most preferably from about 20 nm to about 5 μm, and most preferably from about 50 nm to about 2 m. For example, the microparticles and nanoparticles may have an average size between about 100 and 900 nm, such as about 100, 300, 500, 700, or 900 nm.

As used herein, particle size can be determined by any conventional particle size measuring techniques well known to those skilled in the art. Such techniques include, for example, sedimentation field flow fractionation, photon correlation spectroscopy, light scattering, dynamic light scattering, light diffraction, and disk centrifugation.

Additional Components

The particles of the present invention may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez et al., *Science,* 1998, 281:2013; Niemeyer, C. M., *Angew. Chem. Int. Ed.,* 2003, 42:5796; Waggoner, A. *Methods Enzymol.,* 1995, 246:362; Brus, L. E., *J. Chem. Phys.,* 1993, 79, 5566).

Quantum dots, such as hybrid organic/inorganic quantum dots based on a class of polymers known as dendrimers, may be used in biological labeling, imaging, and optical biosensing systems (Lemon et al., *J. Am. Chem. Soc.,* 2000, 122: 12886). Unlike the traditional synthesis of inorganic quantum dots, the synthesis of these hybrid quantum dot nanoparticles does not require high temperatures or highly toxic, unstable reagents. (Etienne et al., *Appl. Phys. Lett.,* 87:181913, 2005).

Exemplary Uses

The particles and compositions thereof that have numerous applications including in therapeutic methods.

Preferably, the nanoparticles and microparticles or the composition comprising the particles can be used in a method of treating a disease or condition in a subject in need thereof, or a method of reducing the duration or severity of the disease or condition in the subject in need thereof, wherein the disease or condition is treatable with the particles (and optionally with a specific API), comprising administering a composition or a pharmaceutical composition comprising the particles to the subject, thereby treating the disease or condition. Where the particles comprise (for example, encapsulate) an API, the particles can be used in a method of administering or delivering the API to a subject in need thereof and/or for a method of treating a subject suffering from a disease or condition that can be treated with the API. For example, when the API is an anti-inflammatory agent, the particles can be administered to a subject from an inflammatory condition.

In additional aspects, the particles comprise an immunotherapeutic agent and can be used in immunotherapy.

The microparticles and nanoparticles described herein can be used to treat an inflammatory condition. Examples of such diseases and conditions include, but are not limited to, autoimmune hemolytic anemia, idiopathic thrombocytopenic purpura, rheumatoid arthritis, celiac disease, hyper-IgM immunodeficiency, arteriosclerosis, atherosclerosis, coronary artery disease, sepsis, myocarditis, encephalitis, transplant rejection, hepatitis, thyroiditis (e.g. Hashimoto's thyroiditis, Graves disease), osteoporosis, polymyositis, dermatomyositis, Type I diabetes, Type II diabetes, gout, dermatitis, alopecia areata, systemic lupus erythematosus, Sjogren's syndrome, lichen sclerosis, scleroderma, ulcerative colitis, diabetic retinopathy, pelvic inflammatory disease, periodontal disease, arthritis, juvenile chronic arthritis (e.g. chronic iridocyclitis), psoriasis, osteoporosis, nephropathy in diabetes mellitus, asthma, pelvic inflammatory disease, chronic inflammatory liver disease, chronic inflammatory lung disease, lung fibrosis, liver fibrosis, chronic inflammatory lung disease, inflammatory bowel disease (IBD), Crohn's disease, ulcerative colitis, peritonitis, cardiovascular disease, reperfusion injury, ischemia injury, stroke, burns, and other acute and chronic inflammatory diseases of the Central Nervous System (CNS; e.g. multiple sclerosis), gastrointestinal system, the skin and associated structures, the immune system, the hepato-biliary system, or any site in the body where pathology can occur with an inflammatory component. Inflammatory diseases also include diseases involving the gastrointestinal tract and associated tissues (such as ileus, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, coeliac disease, hepatitis, Crohn's disease, enteritis, and Whipple's disease); systemic or local inflammatory diseases and conditions (such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases involving the urogenital system and associated tissues (such as septic abortion, epididymitis, vaginitis, prostatitis, and urethritis); diseases involving the respiratory system and associated tissues (such as bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts, and wheals); diseases involving the cardiovascular system and associated tissues (such as stenosis, restenosis, vasulitis, angiitis, endocarditis, arteritis, atherosclerosis, thrombophlebitis, pericarditis, congestive heart failure, myocarditis, autoimmune myocarditis, myocardial ischemia, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, and Retier's syndrome); as well as various cancers, tumors and proliferative disorders (such as Hodgkins disease); and, in any case the inflammatory or immune host response to any primary disease.

Diseases that can be treated also include allergic disorders or conditions, including allergic disease, allergy, eczema, asthma, allergic rhinitis or skin hypersensitivity.

The disease to be treated can also be a viral infection, including, for example, a hepatitis virus infection, a West Nile virus infection, a flavivirus, an influenza infection, a rhinovirus infection, a papillomavirus infection, a paramyxovirus infection, or a parainfluenza virus infection. Preferably, the viral infection infects the central nervous system of said subject. Preferably, the viral infection causes viral encephalitis or viral meningitis. In yet other aspect, the disease to be treated is a bacterial infection. Exemplary bacterial infections are *staphylococcus* infections, *streptococcus* infections, mycobacterial infections, *bacillus* infections, *Salmonella* infections, *Vibrio* infections, spirochete infections, and *Neisseria* infections. Preferred are bacteria that infect the central nervous system of the subject. Most preferred are bacteria that cause encephalitis or meningitis.

A preferred condition for use in the claimed invention is treating cancers. The cancer to be treated can include Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CML), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In additional embodiment, the cancer is selected from Hodgkin's lymphoma, non-Hodgkin's lymphoma (NHL), indolent non-Hodgkin's lymphoma (iNHL), and refractory iNHL. In certain embodiment, the cancer is indolent non-Hodgkin's lymphoma (iNHL). In some embodiment, the cancer is refractory iNHL. In one embodiment, the cancer is chronic lymphocytic leukemia (CLL). In other embodiment, the cancer is diffuse large B-cell lymphoma (DLBCL).

In certain embodiments, the cancer is a solid tumor is selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophagal cancer, biliary tract cancer, gall bladder cancer, colorectal/appendiceal cancer, squamous cell cancer (e.g., epithelial squamous cell cancer).

Any of the methods of treatment provided may be used to treat cancer at various stages.

By way of example, the cancer stage includes but is not limited to early, advanced, locally advanced, remission, refractory, reoccurred after remission and progressive.

Preferably, the microparticle or nanoparticle of the invention can be used in combination with a second therapeutic that is effective for treating any one of the treatable conditions.

Preferably, the subject is a human patient. Preferably, the subject is a non-human mammal, such as a non-human primate, a livestock animal (horse, mule, cattle, bull, cow, sheep, goat, pig, camel, etc.), a rodent (rabbit, hamster, mouse, rat, etc.), or a pet (cat, dog).

Preferably, the method includes administering the subject composition or pharmaceutical composition comprising the subject microparticles or nanoparticles by any suitable means or routes, such as orally, nasally, intravenously, intramuscularly, ocularly, transdermally, subcutaneously, intratumorally, intravesicularly, intra-articularly, intracranially, and intraperitoneally.

Preferably, about $10^2$ to about $10^{20}$ particles are provided to the individual. Preferably, between about $10^3$ to about $10^{15}$ particles are provided. Preferably, between about 106 to about $10^{12}$ particles are provided. Preferably, between about $10^8$ to about $10^{10}$ particles are provided.

Preferably, the preferred dose is 0.1% solids/ml. Therefore, for 0.5 μm beads, a preferred dose is approximately $4\times10^9$ beads, for 0.05 μm beads, a preferred dose is approximately $4\times10^{12}$ beads, for 3 m beads, a preferred dose is $2\times10^7$ beads. However, a dose that is effective in treating the particular condition to be treated is encompassed by the current invention.

The effectiveness of the microparticles and nanoparticles described herein against the treatable diseases and conditions can be tested using a number of efficacy tests, including suitable animal models.

Pharmaceutical Composition

One aspect of the present invention provides pharmaceutical compositions which comprise the subject microparticles and nanoparticles, and optionally comprise a pharmaceutically acceptable carrier or excipient. Preferably, these compositions optionally further comprise one or more additional therapeutic agents. Alternatively, the subject particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, an immunotherapeutic agent, or a chemotherapeutic agent, or it may be any one of a number of agents undergoing approval in the Food and Drug Administration. It will also be appreciated that certain of the subject particles of present invention can exist in free form for treatment, or where appropriate, as a pharmaceutically acceptable derivative thereof.

Preferably, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The particles can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch.

Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

It will also be appreciated that the nanoparticles and microparticles and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

Preferably, the pharmaceutical compositions containing the particles of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, anti-nausea medications and anti-sickness drugs.

The following examples are given to illustrate the present invention. It should be understood, however, that the invention is not to be limited to the specific conditions or details described in these examples.

EXAMPLES

Example 1. Preparation of PLGA Nanoparticles Having Polysialic Acid on Surface 200 mg PLGA is dissolved in 8 ml ethyl acetate to form a PLGA solution which is mixed with 40 mL 0.5% polyvinyl alcohol (PVA) solution containing 40 milligram of colominic acid and homogenized at 25,000 rpm for 1 minute using an IKA® DIGITAL ULTRA-TURRAX® T25 Homogenizer. The resulting emulsion is poured into a glass container and stirred magnetically at 400 rpm for 3 hours to allow the evaporation of the solvent. The nanoparticles are then washed three times with distilled water before lyophilization. The lyophilized particles are reconstituted in distilled water for the measurement of particle size, size distribution, zeta potential and quantity of polysialic acid on the surface.

Example 2. Preparation of Protein-Loaded PLGA Nanoparticles Having Polysialic Acid on Surface Via a Double-Emulsion Process 200 mg PLGA is dissolved in 4 mL ethyl acetate to form a PLGA solution. A mix solution consisting of 35 ml 2% polyvinyl alcohol (PVA) solution (in water), 1.5 ml of ethyl acetate, and 40 milligrams of colominic acid is prepared. 4 mg of bovine serum albumin (BSA, a model therapeutic protein) is dissolved in 0.4 mL of an aqueous buffer to form the protein solution. The BSA solution is mixed with the PLGA solution and the resulting mix is homogenized using a probe sonicator for 30 seconds. The resulting emulsion is mixed with the PVA/polysialic acid solution and homogenized at 18,000 rpm using an IKA® DIGITAL ULTRA-TURRAX® T25 Homogenizer for 1 minute. The resulting final emulsion is poured into a 250 mL glass flask and the solvent is removed by rotor evaporation at a vacuum of 50 mbar. The BSA loaded particles are washed three times with distilled water and lyophilized. The lyophilized particles are reconstituted in distilled water for the measurement of particle size, size distribution, zeta potential, protein encapsulation efficiency and quantity of polysialic acid on the surface.

Example 3. Preparation of Paclitaxel-Loaded PLGA Nanoparticles Having Polysialic Acid on Surface Via a Single-Emulsion Process 200 mg PLGA and 4 mg paclitaxel are dissolved in 4 mL ethyl acetate to form a PLGA-paclitaxel solution. The PLGA-paclitaxel solution is mixed with 16 mL 2.5% polyvinyl alcohol solution containing 40 milligrams of polysialic acid, and homogenized at 24,000 rpm for 1 minute using an IKA® DIGITAL ULTRA-TURRAX® T25 Homogenizer. The resulting emulsion is poured into a glass container and stirred magnetically at 400 rpm for 4 hours to allow the evaporation of the solvent. The paclitaxel loaded nanoparticles are then washed three times with distilled water and lyophilized. The BSA loaded particles are washed three times with distilled water and lyophilized. The lyophilized particles are reconstituted in distilled water for the measurement of particle size, size distribution, zeta potential, drug encapsulation efficiency and quantity of polysialic acid on the surface.

Example 4. Preparation of Polycaprolactone Nanoparticles Having Polysialic Acid on the Surface 100 mg polycaprolactone (PCL) is dissolved in 6 ml dichloromethane (DCM) to form a PCL solution which is mixed with 40 mL 5% polyvinyl alcohol (PVA) solution containing 40 milligrams of colominic acid and homogenized at 25,000 rpm for 1 minute using an IKA® DIGITAL ULTRA-TURRAX® T25 Homogenizer. The resulting emulsion is poured into a glass container and stirred magnetically at 400 rpm for 3 hours to allow the evaporation of DCM. The nanoparticles are then washed three times with distilled water before lyophilization. The lyophilized particles are reconstituted in distilled water for the measurement of particle size, size distribution, zeta potential and quantity of polysialic acid on the surface.

Example 5. Preparation of a Fluorescently Labeled Oligonucleotide

An antisense oligonucleotide (ASO) targeting a non-coding nuclear RNA, metastasis-associated lung adenocarcinoma transcript 1 (MALAT1) with a primary amine group added at the 5'-position (see FIG. 1) was obtained from Boston Open Labs, Cambridge, MA. Such MALAT1-ASO-5'-amine was reacted with equal molar quantity of a Cy7 near-IR fluorescent dye functionalized with NHS ester. The resulting reaction product is referred to as ASO-Cy7 conjugate.

Example 6. Preparation of Nanoparticles Loaded with the ASO-Cy7 Conjugate and Having Polysialic Acid Presented on the Surface Approximately 50 mg of the ASO-Cy7 conjugate prepared in Example 5 was dissolved in 1 mL distilled water to form an ASO solution. 100 mg of poly (lactide-co-glycolide) (PLGA, ester end-capped) was dissolved in 1 mL ethyl acetate to form a polymer solution. 63.75 mg of ethyl lauroyl arginate (ELA) was dissolved in 1 mL benzyl alcohol to form an ELA solution. Mix 0.5 mL of the polymer solution, 0.2 mL of the ELA solution, 0.3 mL of ethyl acetate, and 0.1 mL of the ASO solution in an 8-mL glass vial. The resulting mixture in the 8-mL vial was probe-sonicated at 90% amplitude for 30 seconds to result in a first emulsion, which was transferred into a 15-mL glass vial containing 5 mL of an aqueous solution consisting of 0.5% poly(vinyl alcohol) (PVA, 89% hydrolyzed), 0.2% Brij-S100-PA-SG (Brij-S100), and 0.5% polysialic acid saturated with appropriate amount of ethyl acetate. The entire mixture was immediately probe-sonicated at 90% amplitude for 60 seconds to result in a second emulsion, which was transferred to a 30 mL beaker and stirred magnetically in a chemical fume hood for 2 hours. Once the particles were formed and hardened, the suspension was washed with 50 mL phosphate buffer saline followed by 50 mL distilled water twice using tangential flow filtration. After purification, the nanoparticles were lyophilized. The nanoparticles obtained were found to have an average particle size of 155.6 nm, a loading of the ASO-Cy7 of 3.9%, and a surface zeta potential of −33.0 mV.

Example 7. Wash Test 50 mg PLGA nanoparticles produced as described in Example 1 are reconstituted in 30 mL deionized water. After brief sonication, the particles are well suspended. A sample is taken for measurement of zeta potential.

To such nanoparticle suspension is then added 300 mL of deionized water. The resulting mixture is concentrated using a tangential flow filtration (TFF) device to 30 mL and zeta potential is measured again. This washing step is repeated four more times, and the resulting zeta potential after each wash is measured and recorded.

While this invention has been particularly shown and described with references to preferred embodiments thereof, it will be understood by those skilled in the art that various changes in form and details may be made therein without departing from the scope of the invention encompassed by the appended claims.

It should be understood that any preferred features of the invention described herein can be combined with any other preferred features, including preferred features described only under one aspect of the invention, and preferred features described only in the examples. Throughout the specification, any and all references to a publicly available document, including any U.S. patent or patent application publication, are specifically incorporated by reference.

What is claimed is:

1. A composition comprising particles presenting sialic acid residues on their surfaces, wherein each particle comprises a biodegradable polymer and a polysialic acid comprising the sialic acid residues, wherein the sialic acid residues are present on the surface of the particles and are not conjugated thereto; and wherein the particles are microparticles or nanoparticles.

2. The composition of claim 1, wherein the biodegradable polymer is selected from the group consisting of: polylactide (PLA), poly (lactide-co-glycolide) (PLGA), copolymers of ethylene glycol and lactide/glycolide (PEG-PLGA), copolymers of ethylene glycol and lactide (PEG-PLA), copolymers of ethylene glycol and glycolide (PEG-PGA), poly (ethylene glycol) (PEG), polycaprolactone (PCL), polyanhydrides (PANH), poly (ortho esters), polycyanoacrylates, poly (hydroxyalkanoate) s (PHAs), poly (sebasic acid), polyphosphazenes, polyphosphoesters, modified poly (saccharide) s, mixtures and copolymers thereof.

3. The composition of claim 2, wherein the biodegradable polymer is PLGA.

4. The composition of claim 1, wherein the particles are nanoparticles.

5. The composition of claim 1, wherein the biodegradable polymer and the polysialic acid form an interpenetrating network.

6. The composition of claim 3, wherein the PLGA and the polysialic acid form an interpenetrating network.

7. The composition of claim 1, wherein the sialic acid residues are selected from the group consisting of Neu5 Ac, Neu5Gc, and Kdn, or a combination thereof.

8. The composition of claim 1, wherein the polysialic acid is a homopolymer.

9. The composition of claim 1, wherein the polysialic acid is colominic acid.

10. The composition of claim 1, wherein the particles further comprise an active agent.

11. The composition of claim 10, wherein the active agent is an active pharmaceutical ingredient selected from the group consisting of small molecules, peptides, proteins, and nucleic acids.

12. The composition of claim 11, wherein the active agent is a nucleic acid selected from the group consisting of DNA, RNA and antisense oligonucleotides.

13. The composition of claim 12 further comprises a cationic complexing agent selected from the group containing small molecule cationic agents, cationic or ionizable lipids, and cationic polymers.

14. The composition of claim 10, wherein the active agent is encapsulated within the particles.

15. The composition of claim 1, wherein the composition further comprises a pharmaceutically acceptable excipient.

16. A method for administration of an active agent to a subject in need thereof comprising administering to said subject the composition of claim 10.

17. The method of claim 16, wherein the active agent is an active pharmaceutical ingredient.

18. The method of claim 16, wherein the active agent is encapsulated within the particles.

19. A method for the treatment of a disease or disorder in a subject in need thereof comprising administering to said subject the composition of claim 11.

20. The method of claim 19, wherein the disease is cancer.

21. The method of claim 19, wherein the active pharmaceutical ingredient is an anti-cancer agent or an immunotherapeutic agent.

22. The method of claim 19, wherein the disease is an autoimmune disease.

* * * * *